United States Patent
Blais et al.

(10) Patent No.: US 12,390,197 B2
(45) Date of Patent: Aug. 19, 2025

(54) METHODS AND SYSTEMS FOR ULTRASOUND IMAGING

(71) Applicant: POLYVALOR, LIMITED PARTNERSHIP, Montréal (CA)

(72) Inventors: Simon Blais, Montréal (CA); Jonathan Poree, Montréal (CA); Jean Provost, Montréal (CA)

(73) Assignee: CORPORATION DE L'ECOLE POLYTECHNIQUE DE MONTREAL, Montreal (CA)

( * ) Notice: Subject to any disclaimer, the term of this patent is extended or adjusted under 35 U.S.C. 154(b) by 31 days.

(21) Appl. No.: 18/019,618

(22) PCT Filed: Aug. 5, 2021

(86) PCT No.: PCT/CA2021/051087
§ 371 (c)(1),
(2) Date: Feb. 3, 2023

(87) PCT Pub. No.: WO2022/027134
PCT Pub. Date: Feb. 10, 2022

(65) Prior Publication Data
US 2023/0301630 A1 Sep. 28, 2023

Related U.S. Application Data

(60) Provisional application No. 63/062,107, filed on Aug. 6, 2020.

(51) Int. Cl.
*A61B 8/08* (2006.01)
*A61B 8/00* (2006.01)
(Continued)

(52) U.S. Cl.
CPC .............. *A61B 8/481* (2013.01); *A61B 8/461* (2013.01); *A61N 7/02* (2013.01); *A61N 2007/0039* (2013.01)

(58) Field of Classification Search
CPC ....... A61B 8/481; A61B 8/461; A61B 8/0808; A61B 8/0891; A61N 7/02; A61N 2007/0039; G01S 7/52022; G01S 7/52039
See application file for complete search history.

(56) References Cited

U.S. PATENT DOCUMENTS

| 5,577,505 A | 11/1996 | Brock-Fisher et al. |
| 2006/0052701 A1* | 3/2006 | Carter ................. A61B 8/4281 601/2 |

(Continued)

FOREIGN PATENT DOCUMENTS

| WO | WO-2010103469 A1 * | 9/2010 | ......... A61B 17/2256 |
| WO | WO-2011027264 A1 * | 3/2011 | ........... A61B 5/6814 |

OTHER PUBLICATIONS

M. Tanter and M. Fink, "Ultrafast imaging in biomedical ultrasound", IEEE transactions on ultrasonics, ferroelectrics, and frequency control. vol. 61(1), pp. 102-119. 2014.

(Continued)

*Primary Examiner* — Alexei Bykhovski
(74) *Attorney, Agent, or Firm* — NORTON ROSE FULBRIGHT CANADA LLP

(57) ABSTRACT

There is provided a method for ultrasound imaging comprising applying an ultrasound modulation wave at a fixed frequency $F_1$ and a period $P_1$ to a target in a body, the body having received an injection of microbubbles through a fluid, the modulation wave causing the microbubbles to undergo stable acoustic cavitation, emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, detecting reflections of the ultrasound pulses by the microbubbles after each emission for a duration correspond- (Continued)

ing to a maximum depth of the target, and forming ultrasound images from the reflections.

20 Claims, 16 Drawing Sheets

(51) Int. Cl.
    *A61N 7/02*     (2006.01)
    *A61N 7/00*     (2006.01)

(56) References Cited

U.S. PATENT DOCUMENTS

| | | | |
|---|---|---|---|
| 2013/0053691 | A1 | 2/2013 | Kawabata et al. |
| 2014/0236005 | A1* | 8/2014 | Chen .................. A61B 8/5246 600/431 |
| 2016/0174943 | A1* | 6/2016 | Deng .................. A61B 8/5207 600/440 |
| 2017/0347990 | A1* | 12/2017 | Watanabe ........... G01S 7/52022 |
| 2019/0351261 | A1* | 11/2019 | Levy ..................... G01R 33/561 |
| 2021/0038917 | A1* | 2/2021 | Karasawa .............. G06F 3/147 |
| 2021/0251599 | A1* | 8/2021 | Torp ........................ A61B 8/461 |
| 2022/0305298 | A1* | 9/2022 | Anquez .................... A61N 7/02 |

OTHER PUBLICATIONS

T. Deffieux, C. Demene, M. Pernot, M. Tanter, "Functional ultrasound neuroimaging: a review of the preclinical and clinical state of the art", Current opinion in neurobiology. vol. 50, pp. 128-135, 2018.

N. De Jong, A. Bouakaz, P. Frinking, "Basic acoustic properties of microbubbles", Echocardiography. vol. 19(3), pp. 229-240, 2002.

C.X. Deng, F.L. Lizzi, "A review of physical phenomena associated with ultrasonic contrast agents and illustrative clinical applications", Ultrasound in medicine & biology. vol. 28(3), pp. 277-286, 2002.

Victor Mor-Avi, Enrico G. Caiani, Keith A. Collins, Claudia E. Korcarz, James E. Bednarz, Roberto M. Lang, "Combined assessment of myocardial perfusion and regional left ventricular function by analysis of contrast-enhanced power modulation images", Circulation. vol. 4, pp. 352-357, 2001.

R.J. Eckersley, C.T. Chin, P.N. Burns, "Optimising phase and amplitude modulation schemes for imaging microbubble contrast agents at low acoustic power", Ultrasound in medicine & biology. vol. 31(2), pp. 213-219, 2005.

O. Couture, S. Bannouf, G. Montaldo, J-F. Aubry, M. Fink, M. Tanter. "Ultrafast imaging of ultrasound contrast agents". Ultrasound in medicine & biology, 35(11), pp. 1908-1916, 2009.

F. Forsberg, W.T. Shi, B.B. Goldberg, "Subharmonic imaging of contrast agents", Ultrasonics. vol. 38 (1-8), pp. 93-98, 2000.

R.C. Gessner, C.B. Frederick, F.S. Foster, P.A. Dayton, "Acoustic angiography: a new imaging modality for assessing microvasculature architecture", Journal of Biomedical Imaging. vol. 2013, ID 936593, 2013.

O. Couture, B. Besson, G. Montaldo, M. Fink, M. Tanter, "Microbubble ultrasound super-localization imaging (MUSLI)", in Ultrasonics Symposium, Orlando, FL, USA, 2011, pp. 1285-1287.

C. Errico, J. Pierre, S. Pezet, Y. Desailly, Z. Lenkei, O. Couture, M. Tanter, "Ultrafast ultrasound localization microscopy for deep super-resolution vascular imaging", Nature. vol. 527(7579), pp. 499-502, 2015.

O. Couture, V. Hingot, B. Heiles, P. Muleki-Seya, M. Tanter, "Ultrasound localization microscopy and super-resolution: A state of the art", IEEE transactions on ultrasonics, ferroelectrics, and frequency control. vol. 65(8), pp. 1304-1320, 2018.

Y. Desailly, A-M. Tissier, J-M. Correas, F. Wintzenrieth, M. Tanter, O. Couture, "Contrast enhanced ultrasound by real-time spatiotemporal filtering of ultrafast images", Physics in Medicine & Biology. vol. 62(1), pp. 31-42. 2017.

Dilantha B. Ellegala, Howard Leong-Poi, Joan E. Carpenter, Alexander L. Klibanov, Sanjiv Kaul, Mark E. Shaffrey, Jiri Sklenar, Jonathan R. Lindner, "Imaging tumor angiogenesis with contrast ultrasound and microbubbles targeted to $\alpha v\beta 3$", Circulation. vol. 108, pp. 336-341, 2003.

G.E.R. Weller, M.K.K. Wong, R.A. Modzelewski, E. L, A.L. Klibanov, W.R. Wagner, F.S. Villanueva, "Ultrasonic imaging of tumor angiogenesis using contrast microbubbles targeted via the tumor-binding peptide arginine-arginine-leucine", Cancer research. vol. 65(2), pp. 533-539, 2005.

J.K. Willman, R. Paulmurugan, K. Chen, O. Gheysens, M. Rodriguez-Porcel, A.M. Lutz, I.Y. Chen, X. Chen, S.S. Gambhir, "US imaging of tumor angiogenesis with microbubbles targeted to vascular endothelial growth factor receptor type 2 in mice", Radiology. vol. 246(2), pp. 508-518, 2008.

P. Marmottant, S. Van Dermeer, M. Emmer, M. Versluis, N. De Jong, S. Hilgenfeldt, D. Lohse, "A model for large amplitude oscillations of coated bubbles accounting for buckling and rupture", Journal of Acoustical Society of America. vol. 118(6), pp. 3499-3505, 2005.

C.X. Deng, F.L. Lizzi, A. Kalisz, A. Rosado, R.H. Silverman, D.J. Coleman, "Study of ultrasonic contrast agents using a dual-frequency band technique", Ultrasound in medicine & biology. vol. 26(5), pp. 819-831, 2000.

A. Bouakaz, N. De Jong, "New contrast imaging method using double frequency exposure", In Ultrasonics Symposium, Montreal, QC, Canada, 2004, pp. 339-342.

M. Emmer, H.J. Vos, M. Versluis, N. De Jong, "Radial modulation of single microbubbles", IEEE transactions on ultrasonics, ferroelectrics, and frequency control. vol. 56(11), pp. 2370-2379, 2009.

E. Chérin, J. Brown, S-E. Måsøy, H. Shariff, R. Karshafian, R. Williams, P.N. Burns, F.S. Foster, "Radial modulation imaging of microbubble contrast agents at high frequency", Ultrasound in medicine & biology. vol. 34(6), pp. 949-962, 2008.

H.H. Shariff, P.D. Bevan, R. Karshafian, R. Williams, P.N. Burns, "Radial Modulation Imaging: Raising the Frequency for Contrast Imaging", In Ultrasonics Symposium, Vancouver, BC, Canada, 2006, pp. 104-107.

B.A. Angelsen, R. Hansen, "Surf Imaging—A new method for ultrasound contrast agent imaging", In Ultrasonics Symposium, New-York, NY, USA, 2007, pp. 531-541.

R. Hansen, B.A. Angelsen, "Surf imaging for contrast agent detection", IEEE transactions on ultrasonics, ferroelectrics, and frequency control. vol. 56(2), pp. 280-290, 2009.

R. Hansen, S-E. Måsøy, T.A. Tangen, B.A. Angelsen, "Nonlinear propagation delay and pulse distortion resulting from dual frequency band transmit pulse complexes", The Journal of the Acoustical Society of America. vol. 129(2), pp. 1117-1127, 2011.

F.T.H. Yu, F.S. Villanueva, X. Chen, "Radial modulation contrast imaging using a 20-MHz single element intravascular ultrasound catheter", IEEE transactions on ultrasonics, ferroelectrics, and frequency control. vol. 61(5), pp. 779-791, 2014.

S-E. Masoy, O. Standal, P. Nasholm, T.F. Johansen, B.A. Angelsen, R. Hansen, "Surf imaging: In vivo demonstration of an ultrasound contrast agent detection technique", IEEE transactions on ultrasonics, ferroelectrics, and frequency control. vol. 55(5), pp. 1112-1121. 2008.

M. Schneider, "Characteristics of SonoVueTM", Echocardiography. vol. 16(7), pp. 743-746, 1999.

A. Needles, M. Arditi, N.G. Rognin, J. Mehi, T. Coulthard, C. Bilan-Tracey, E. Gaud, P. Frinking, D. Hirson, F.S. Foster, "Nonlinear contrast imaging with an array-based micro-ultrasound system", Ultrasound in medicine & biology. vol. 36(12), pp. 2097-2106, 2010.

P. Muleki-Seya, K. Xu, M. Tanter, O. Couture, "Ultrafast radial modulation imaging", IEEE Trans Ultrason Ferroelectr Freq Control, Mar. 2020; 67(3):598-611.

Novell, A., Kamimura, H.A.S., Cafarelli, A. et al, "A new safety index based on intrapulse monitoring of ultra-harmonic cavitation during ultrasound-induced blood-brain barrier opening procedures", Scientific Reports, 2020 (2020), pp. 1-12.

(56) References Cited

OTHER PUBLICATIONS

Shanei A, Sazgarnia A, "An overview of therapeutic applications of ultrasound based on synergetic effects with gold nanoparticles and laser excitation", Iran Journal of Basic Medical Sciences, Aug. 22, 2019 (Aug. 22, 2019), pp. 848-855.

\* cited by examiner

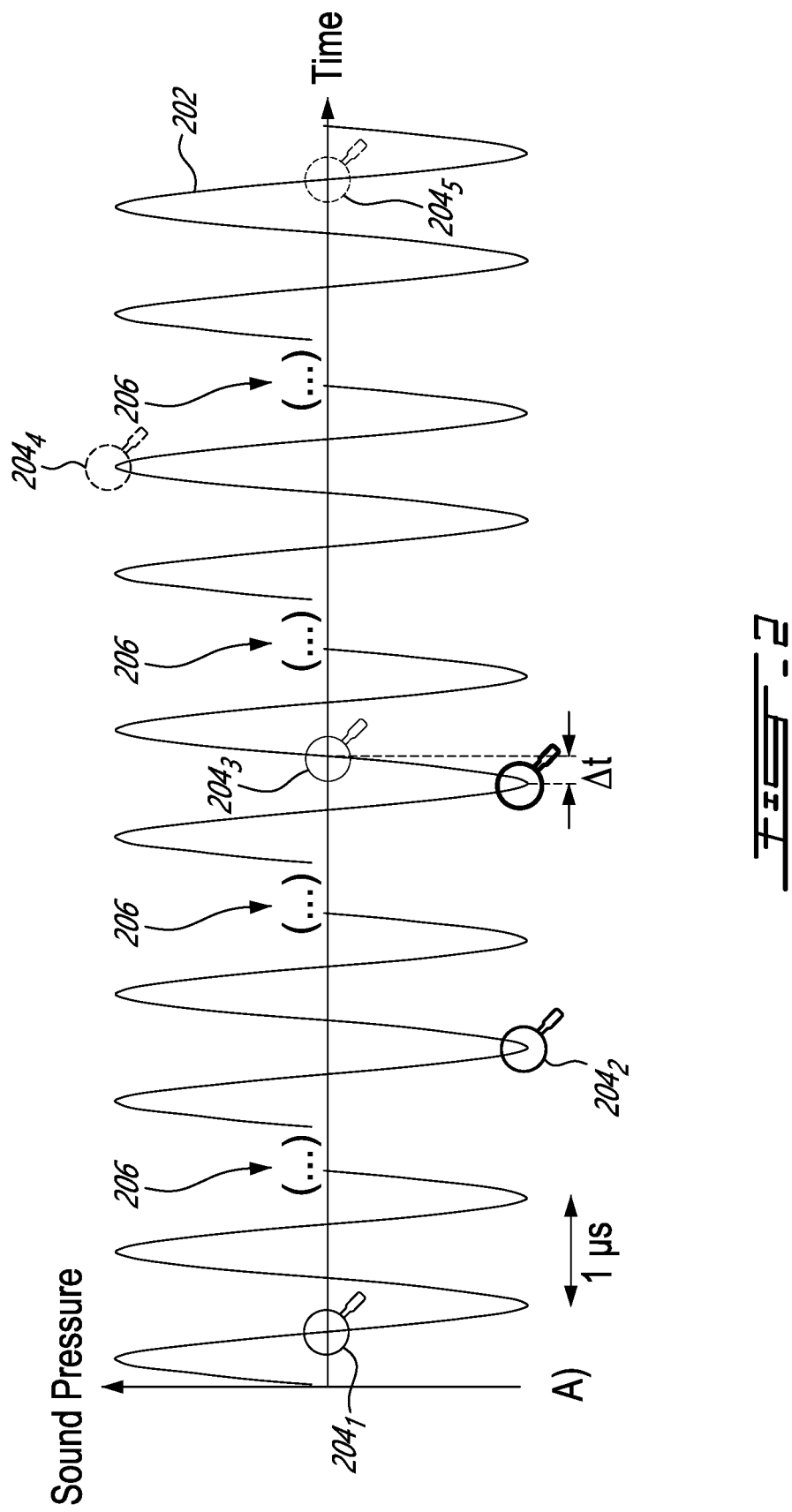

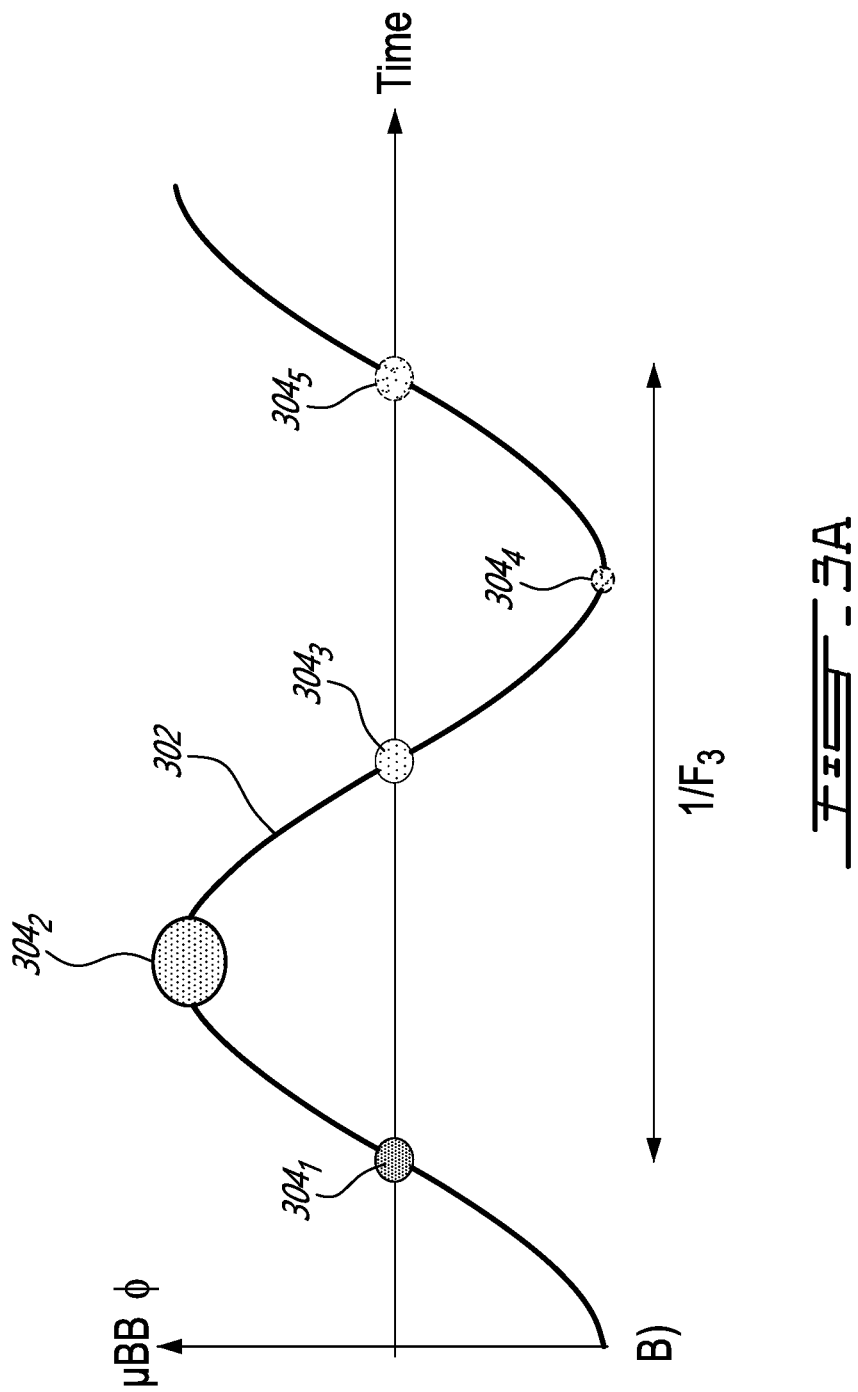

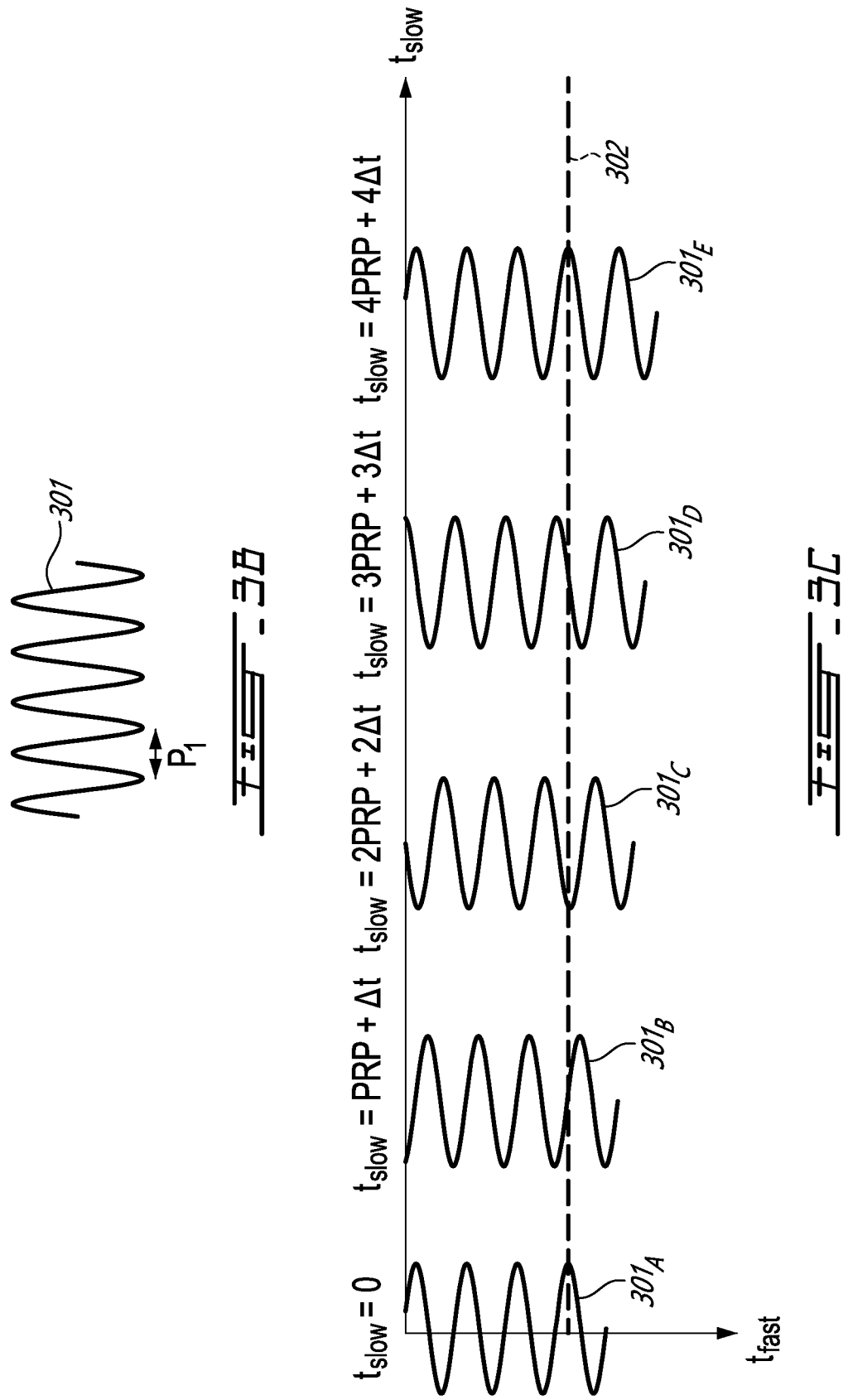

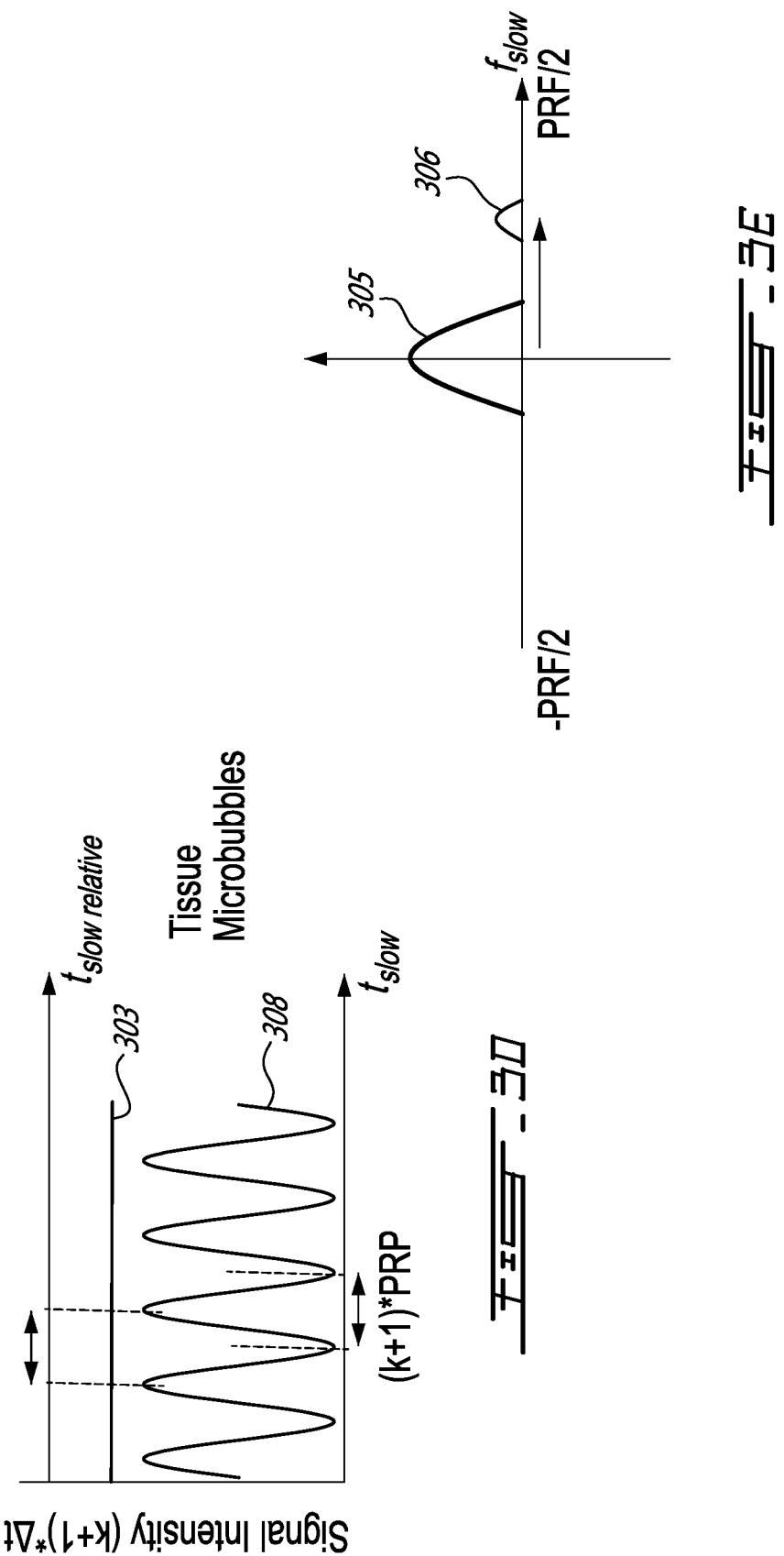

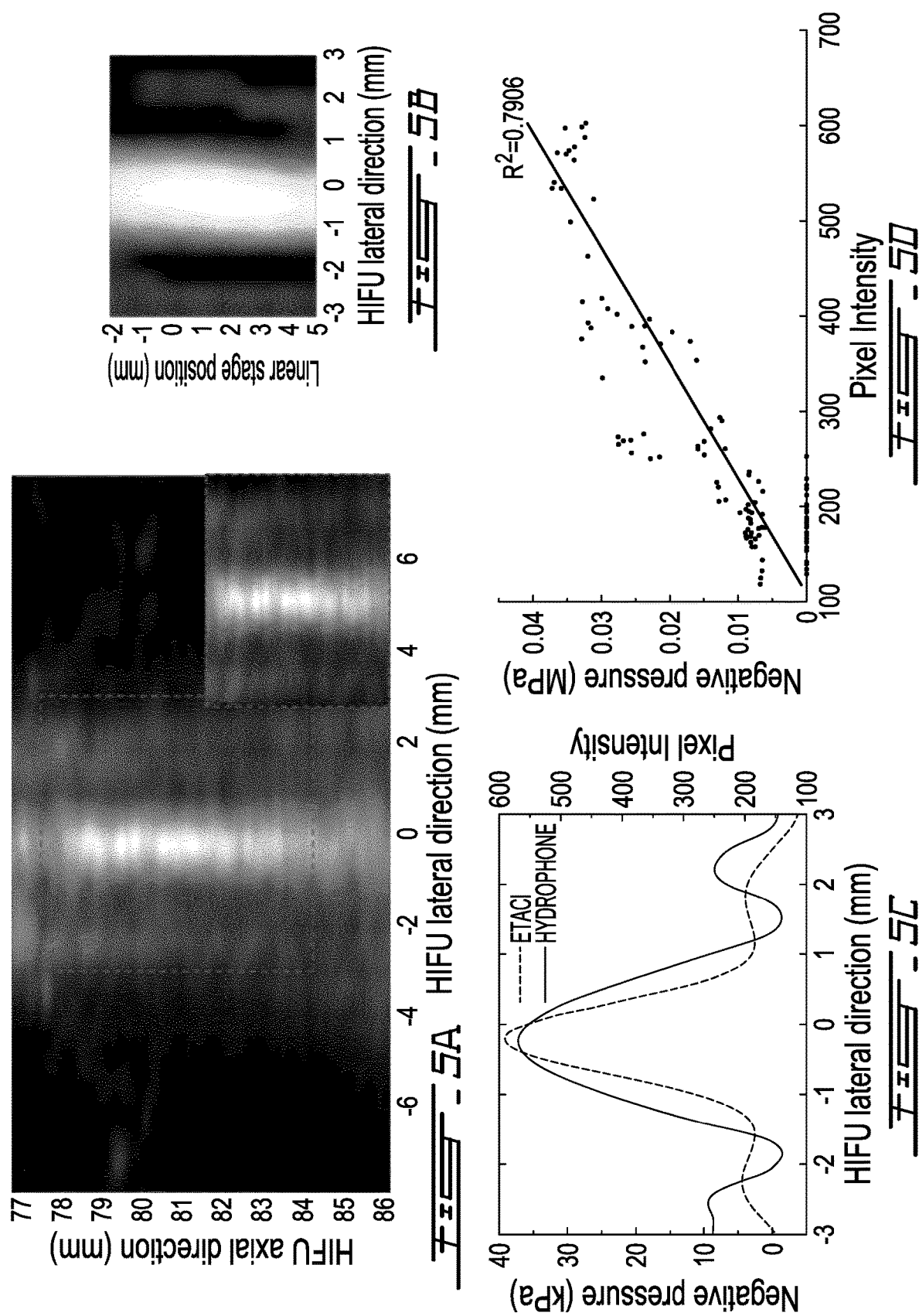

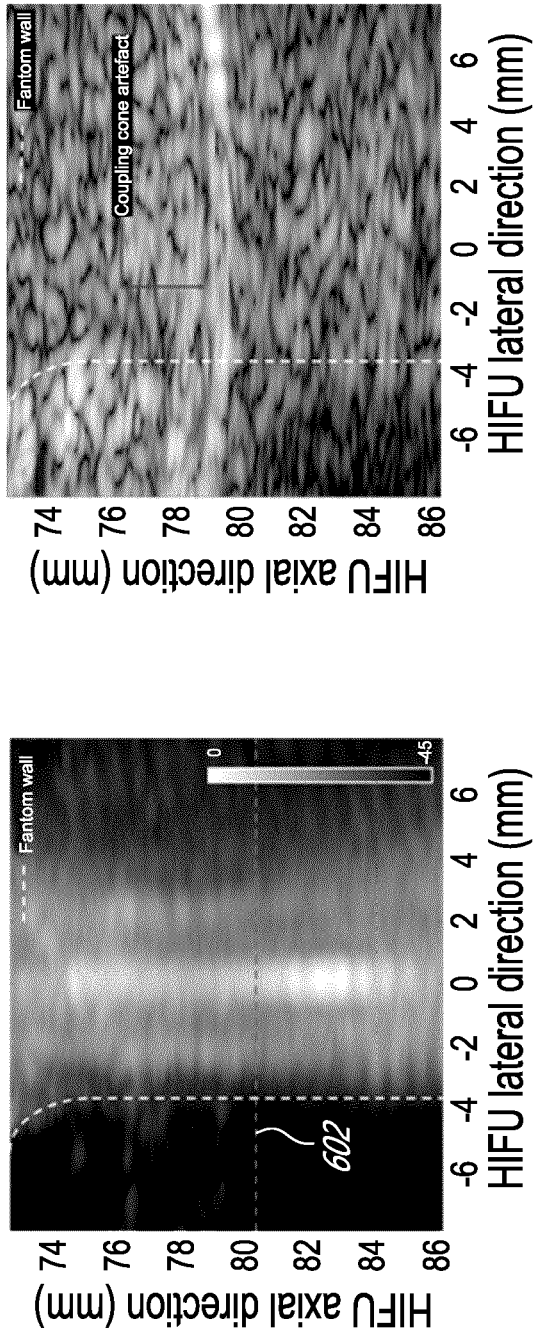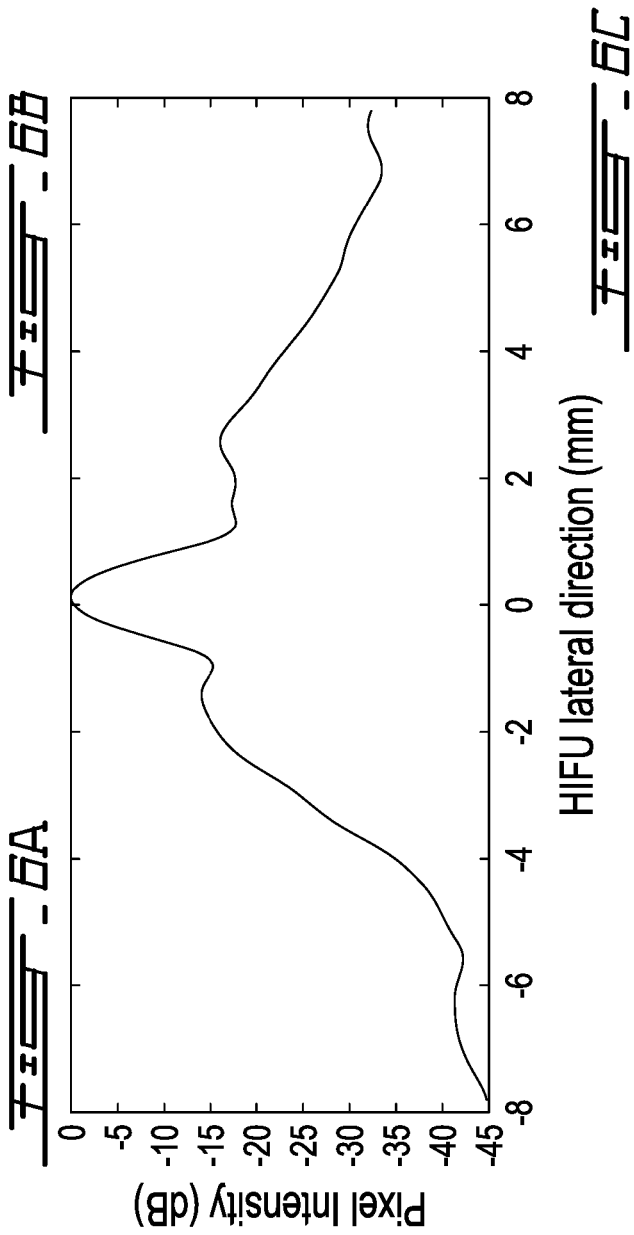
FIG. 6A
FIG. 6B
FIG. 6C

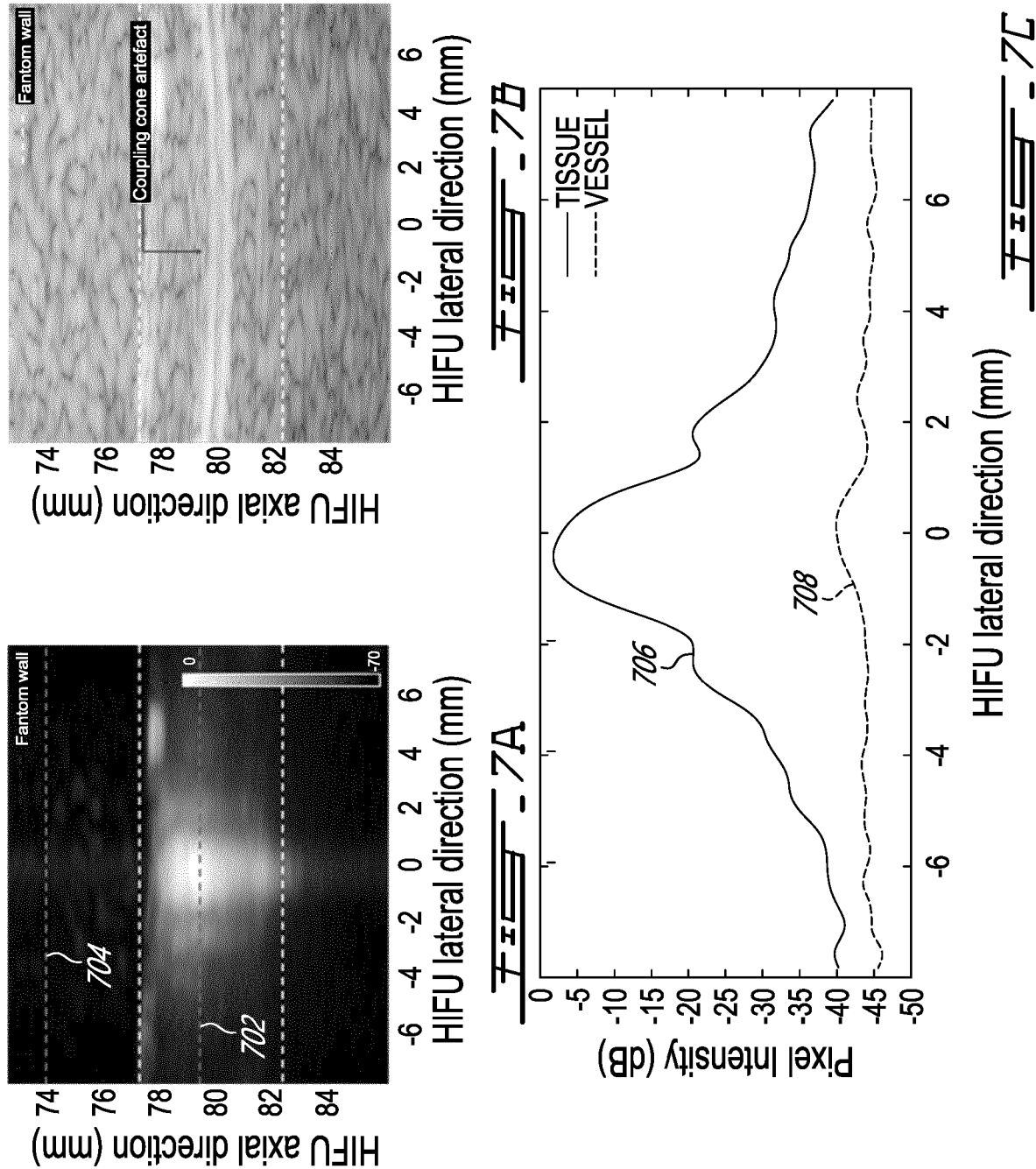

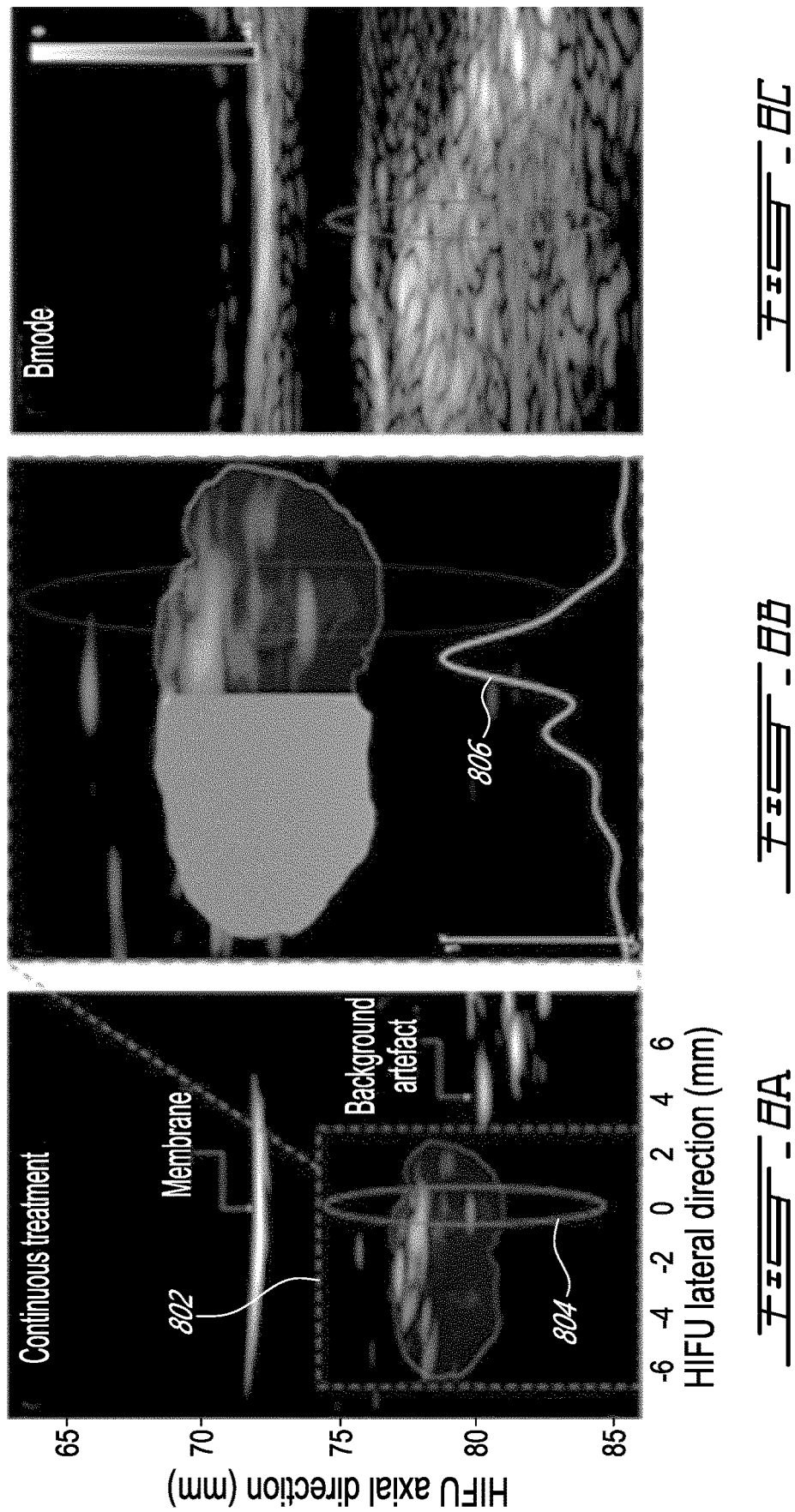

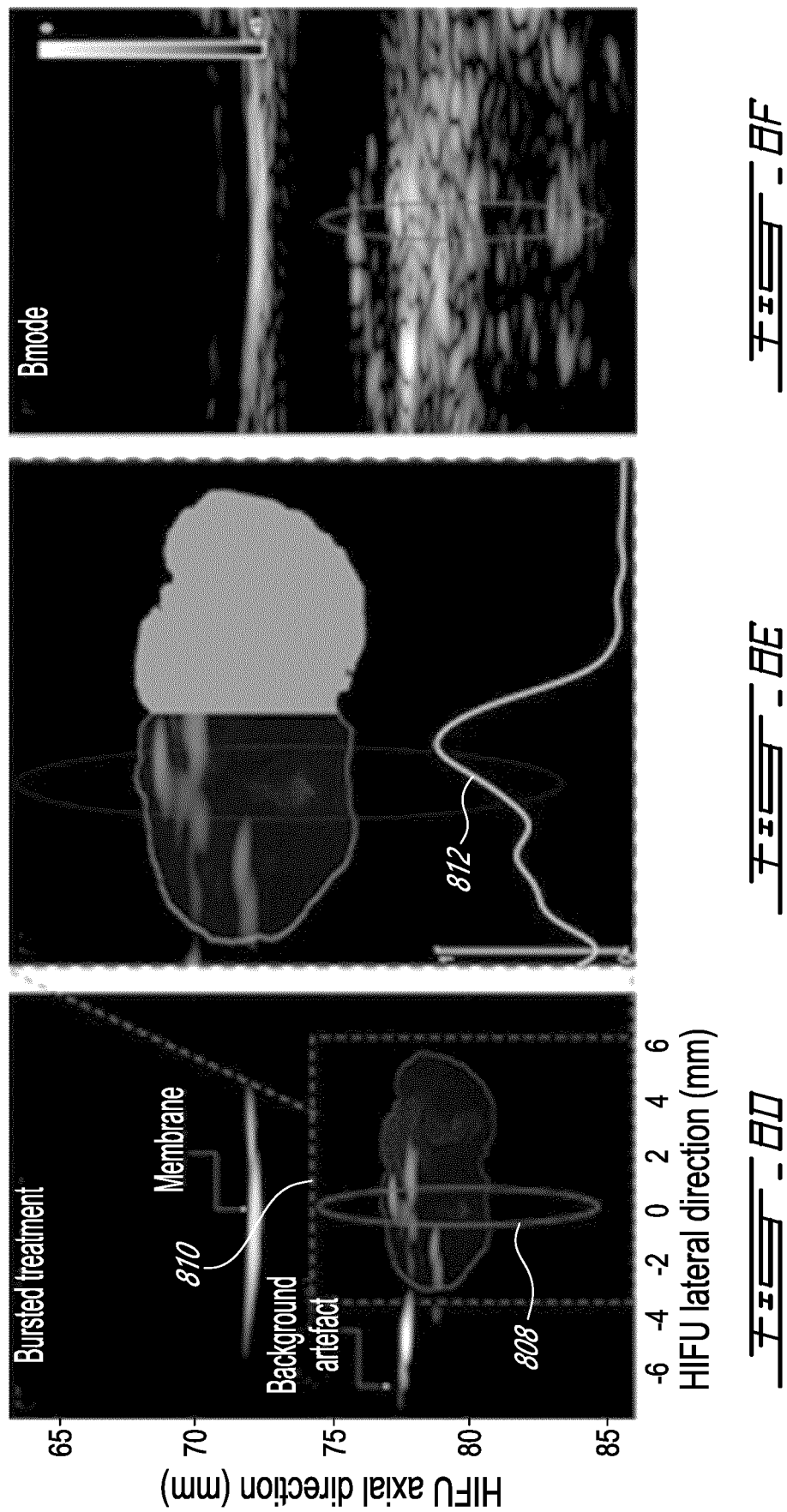

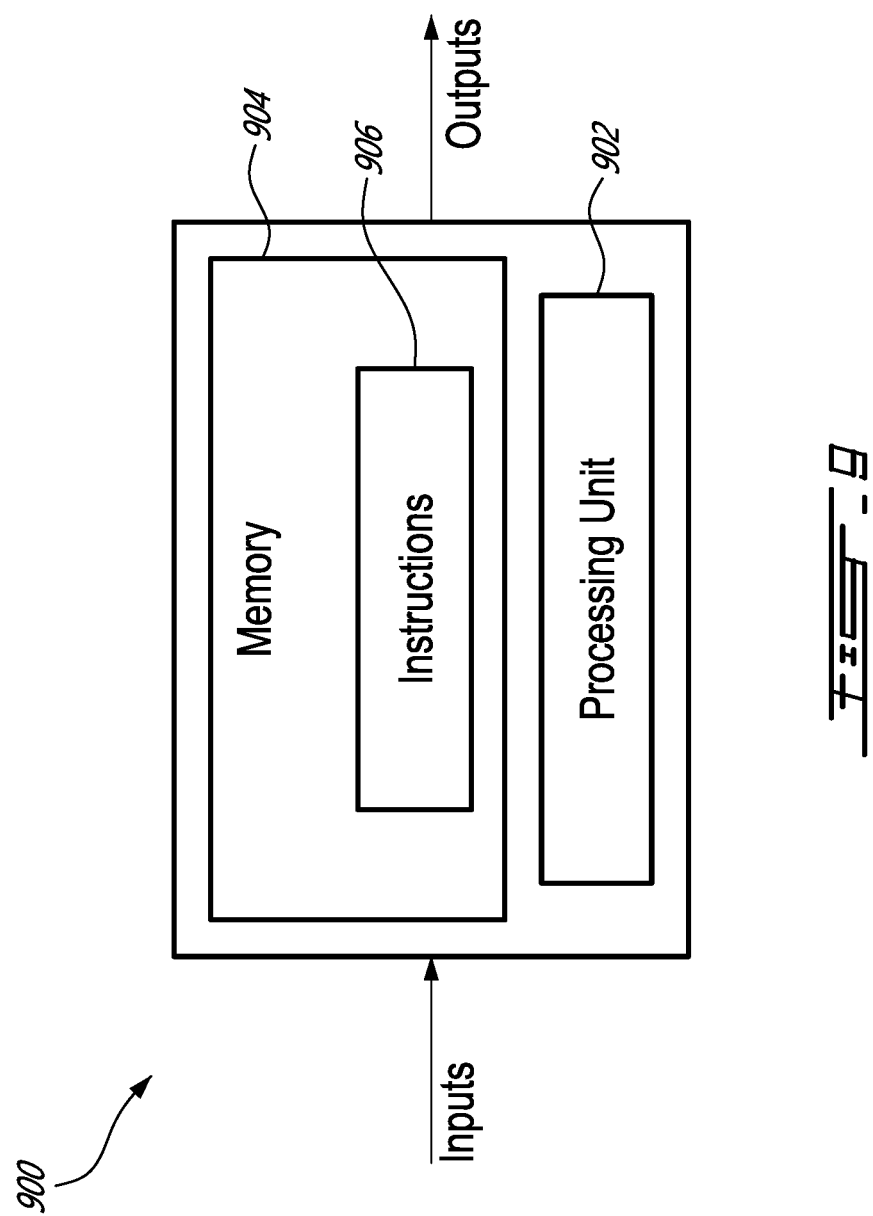

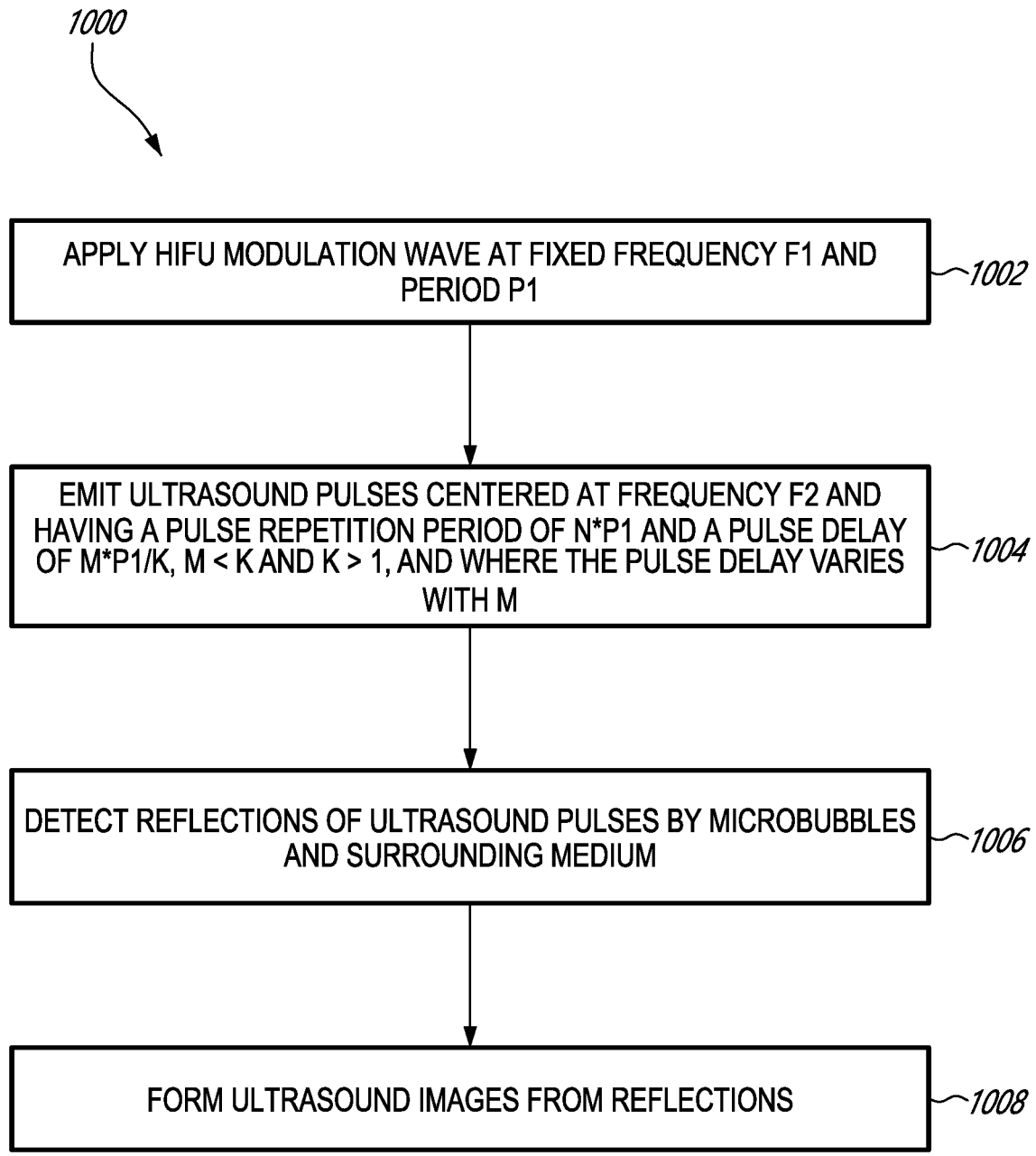

METHODS AND SYSTEMS FOR ULTRASOUND IMAGING

CROSS-REFERENCE TO RELATED APPLICATIONS

The present application is a United States National Stage of International Application No. PCT/CA2021/051087, filed on Aug. 5, 2021, which claims the benefit of U.S. Provisional Patent Application No. 63/062,107 filed on Aug. 6, 2020, the contents of which are hereby incorporated by reference in their entirety.

TECHNICAL FIELD

The present disclosure relates generally to imaging, and more particularly to ultrasound imaging of injected microbubbles in stable acoustic cavitation.

BACKGROUND OF THE ART

Due to the aging of the population, neurological disorders are becoming more prevalent. Such disorders are difficult to treat using standard drugs due to the blood-brain barrier acting as a very selective filter to molecules. The blood-brain barrier can be temporarily rendered permeable using High Intensity focused ultrasounds (HIFU) in combination with microbubbles. Indeed, the microbubbles, when injected into the blood stream, resonate when they are under the effect of ultrasonic modulations. When stable cavitation is present, the blood-brain barrier can be temporarily opened. However, in the presence of inertial cavitation, the implosion of the microbubbles can cause irreversible tissue damage. In addition, the skull alters the propagation of HIFU and can cause a focal point shift, which makes it crucial to monitor the pressure field to ensure its positioning is correct.

Ultrasound Localization Microscopy is an imaging modality that enables the mapping of the microvasculature at depth and in vivo by detecting and localizing with a sub-wavelength accuracy and precision individual microbubbles injected in the bloodstream over a large number of ultrasound images. In order to do so, the background signal originating from tissue, blood, etc., must be removed prior to detecting microbubbles. While multiple methods exist for such background removal, the user must typically choose between high contrast of fast flowing microbubbles or lower contrast and frame rate to detect slow-moving microbubbles.

Therefore, improvements are needed.

SUMMARY

In accordance with a broad aspect, there is provided a method for ultrasound imaging comprising applying an ultrasound modulation wave at a fixed frequency $F_1$ and a period $P_1$ to a target in a body, the body having received an injection of microbubbles through a fluid, the modulation wave causing the microbubbles to undergo stable acoustic cavitation, emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, detecting reflections of the ultrasound pulses by the microbubbles after each emission for a duration corresponding to a maximum depth of the target, and forming ultrasound images from the reflections.

In some embodiments, forming the ultrasound images comprises performing a Fourier analysis in slow time to compute a power spectrum of pixel intensity oscillation.

In some embodiments, the modulation wave is a high intensity focused ultrasound (HIFU).

In some embodiments, the body is an organ.

In some embodiments, forming the ultrasound images comprises forming X sets of Y images, where each detection of a reflection produces one of the images Y, and the Y images are grouped into the X sets.

In some embodiments, the method further comprises generating a global image of a position of the modulation wave over time from the X sets of Y images.

In some embodiments, k<10.

In some embodiments, applying the ultrasound modulation wave comprises applying a treatment beam to the target in the body.

In some embodiments, forming the ultrasound images comprises forming the ultrasound images in real-time and displaying the ultrasound images.

In some embodiments, the method further comprises displacing the modulation wave from a first position to a second position, and confirming the displacing from updated ultrasound images.

In accordance with another broad aspect, there is provided an imaging system comprising a modulation wave generator coupled to an ultrasound transducer configured for emitting a modulation wave at a fixed frequency $F_1$ and a period $P_1$ to a target in a body, the body having received an injection of microbubbles through a fluid, the modulation wave causing the microbubbles to undergo stable acoustic cavitation, and an imaging device coupled to at least one probe and configured for emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, detecting reflections of the ultrasound pulses by the microbubbles after each emission for a duration corresponding to a maximum depth of the target, and forming ultrasound images from the reflections.

In some embodiments, forming the ultrasound images comprises performing a Fourier analysis in slow time to compute a power spectrum of pixel intensity oscillation.

In some embodiments, the modulation wave is a high intensity focused ultrasound (HIFU).

In some embodiments, the body is an organ.

In some embodiments, forming the ultrasound images comprises forming X sets of Y images, where each detection of a reflection produces one of the images Y, and the Y images are grouped into the X sets.

In some embodiments, the imaging device is further configured for generating a global image of a position of the modulation wave over time from the X sets of Y images.

In some embodiments, k<10.

In some embodiments, the ultrasound modulation wave is a treatment beam.

In some embodiments, forming the ultrasound images comprises forming the ultrasound images in real-time and displaying the ultrasound images.

In accordance with yet another broad aspect, there is provided a method for applying a treatment beam to a subject. The method comprises applying the treatment beam as an ultrasound modulation wave at a fixed frequency $F_1$ and a period $P_1$ to a target in subject, the subject having received an injection of microbubbles through a fluid, the modulation wave causing the microbubbles to undergo stable acoustic cavitation, emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, detecting reflections of the ultrasound pulses by the microbubbles after each emission for a duration corresponding to a maximum depth of the target, forming ultrasound images from the reflections, displaying the ultrasound images as the treatment beam is applied, and adjusting a location of the treatment beam based on the ultrasound images.

Features of the systems, devices, and methods described herein may be used in various combinations, in accordance with the embodiments described herein.

BRIEF DESCRIPTION OF THE DRAWINGS

Reference is now made to the accompanying figures in which:

FIG. 2 is a graph of an example modulation wave;

FIGS. 3A-3F graphically illustrate the desynchronization of a modulation wave relative to imaging pulse timing;

FIGS. 5A-5D show high intensity focused ultrasound beam profile mapping in free field at 0.04 MPa peak negative pressure and hydrophone mapping of the same region;

FIGS. 6A-6C show HIFU pressure field and tissue suppression characterisation;

FIGS. 7A-7C show pressure field mapping over the longitudinal section of a vessel in a tissue mimicking flow phantom;

FIGS. 8A-8H show compounded pressure field mapping images of continuous and burst high intensity focused ultrasound blood-brain barrier opening treatment on the right and left sides of the brain;

FIG. 9 is a block diagram of an example computing device; and

FIG. 10 is a flowchart of an example method for ultrasound imaging.

It will be noted that throughout the appended drawings, like features are identified by like reference numerals.

DETAILED DESCRIPTION

There are described herein methods and systems that may be used within the context of diagnostic and/or therapeutic ultrasound. In particular, acoustic cavitation of microbubbles is used to determine and visualize in real time the position of an ultrasonic beam. The ultrasonic beam is a modulation wave that causes pressure changes in the microbubbles, which leads to changes in size of the microbubbles. An imaging pulse is synchronized with the modulation wave to extract the backscattering power of the microbubbles (that is related to its size) and allow characterization of the ultrasonic beam. Knowing that the backscattered signal of the tissue over time stays relatively constant, the microbubbles may be differentiated from the tissue by the variability of the signal in the slow time dimension.

Figure 1:
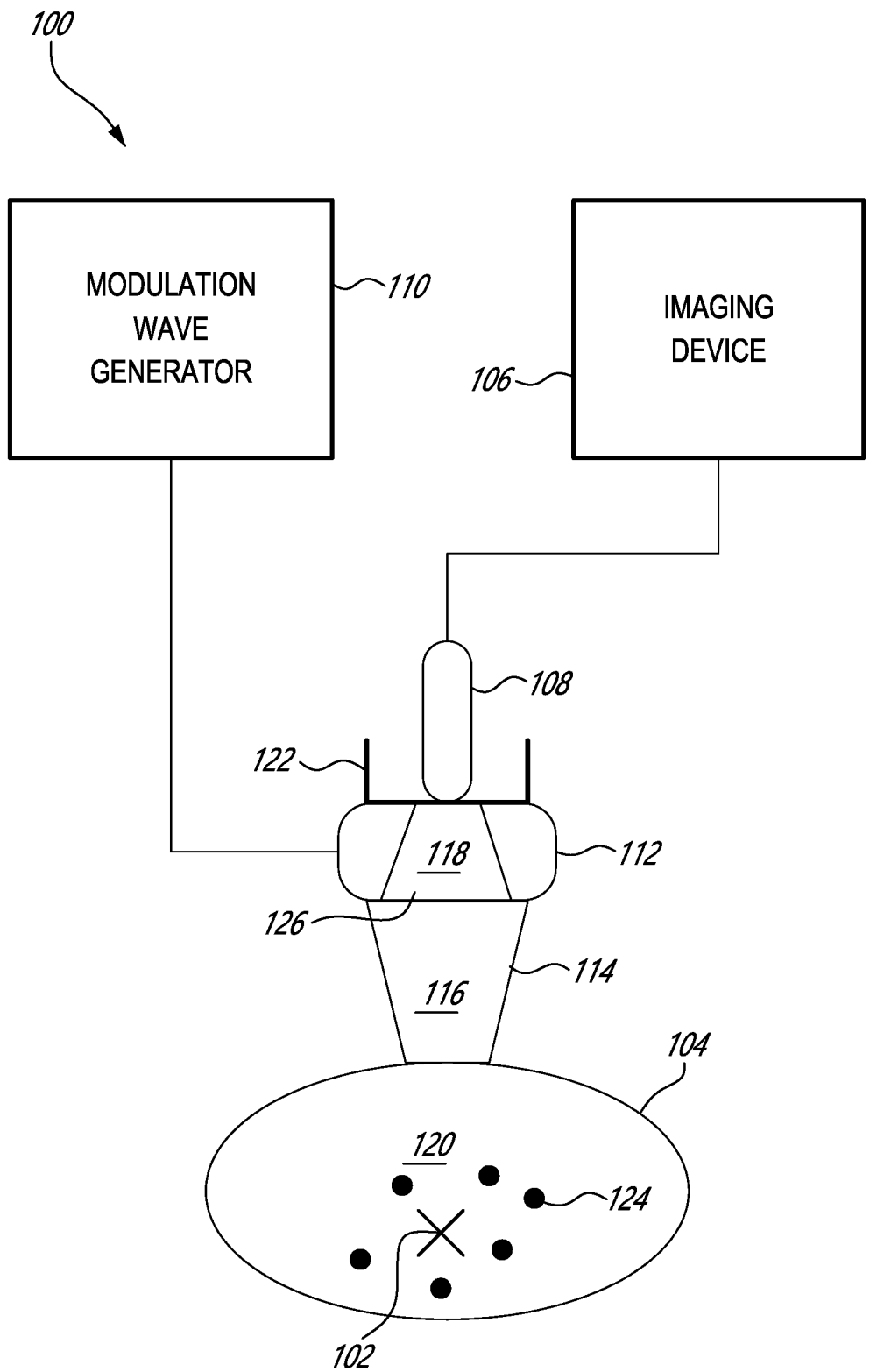
FIG. 1 is a schematic diagram of an example setup for ultrasound imaging.

With reference to FIG. 1, there is illustrated a setup 100 for ultrasound imaging of a target 102, contained in a body 104 having a medium 120 therein. Microbubbles 124, injected into the body 104 via a fluid, surround the target 102 and may act as a contrast agent for the ultrasound imaging.

In some embodiments, the body 104 is biological, such as an organ, the medium 120 is tissue, and the microbubbles are injected through the blood stream. For example, the body may be a brain, a heart, or other organ. In some embodiments, the body 104 is non-biological, such as a tank or other recipient, and the matter is a fluid, such as water. Other embodiments may apply, depending on practical implementations.

An imaging device 106 generates imaging ultrasonic pulses and emits the pulses toward the target via a probe 108. The probe 108 may be supported inside a holder 122 or otherwise positioned relative to the body 104. The ultrasound pulses are reflected by the microbubbles 124 and the surrounding medium 120 and these reflections are detected by the probe 108. Although illustrated as a single probe 108 that emits and detects, two separate probes may be provided, one for emission and one for detection.

In some embodiments, a modulation wave generator 110 is coupled to a High Intensity Focused Ultrasound (HIFU) transducer 112. The modulation wave generator 110 may comprise, for example, a function generator and an amplifier. The modulation wave generator 110 generates an ultrasonic modulation wave that is directed toward the target 102 via the HIFU transducer 112, causing acoustic cavitation of the microbubbles 124 as they come into contact with the pressure field generated by the modulation wave. The amplitude of the ultrasound pulses reflected by the microbubbles 124 thus varies as a function of the acoustic pressure applied to the microbubbles 124 by the modulation wave. Although described herein for HIFU, the method may be used to map the output pressure field of any given probe regardless of its type (HIFU or imaging array probes such as linear arrays or matrix arrays).

In some embodiments, the probe 108 is positioned above the HIFU transducer 112 and aligned with a passage 126 provided therein. The passage 126 is filled with a coupling agent 118 to allow the ultrasound pulses to travel therethrough. Also in some embodiments, a coupling device 114 is provided between the HIFU transducer 112 and the body 104 to couple the modulation wave and the ultrasound pulses with the body 104. A coupling agent 116, which may be the same or different from the coupling agent 118, is contained inside the coupling device 114. The coupling device 114 may be composed of various materials, such as but not limited to polycarbonate. Examples of coupling agents that may be used are water, gel, mineral oil, and white petrolatum. It will be appreciated that the configuration illustrated in FIG. 1 for the setup 100 is exemplary only and may vary. For example, the HIFU transducer 112 may be placed directly into the body 104 if the body is a tank and the matter 120 is water. Also alternatively, the coupling device 116 may be omitted or replaced with a coupling agent applied directly to a surface of the body 104. Other embodiments are also contemplated.

FIG. 2 illustrates an example modulation wave 202 as applied by the HIFU transducer 212. The wave 202 has a fixed frequency $F_1$ and a period $P_1$. In some embodiments, $F_1$=1 MHz and $P_1$=1 µs, but these values are exemplary and may vary. The imaging ultrasonic pulses are centered at a Frequency $F_2$ and offset in time by $\Delta t$ in order to sample the microbubbles at different states of oscillation, where $\Delta t$ is smaller than the period $P_1$ of the modulation wave 202 and varies over time. In order to allow sufficient time for the ultrasonic imaging pulses to travel from the probe 108 to the microbubbles 124 and back to the probe 108, an additional offset is added in between the pulses, such that samples are acquired from different cycles of the modulation wave 202. Indeed, the modulation wave 202 will impact the microbubbles 124 in a cyclical manner, meaning that high- and low-pressure fields will be felt by the microbubbles 124 repetitively at regular intervals, through an oscillation cycle. Therefore, the imaging ultrasonic pulses may be generated with a pulse interval that causes the sampling to occur over different cycles of the modulation wave 202, while skipping entire cycles 206 of the modulation wave 202. Accordingly, the pulse interval, also referred to as pulse repetition period (PRP), may be represented as:

$$PRP = n*P_1$$

And a pulse delay ($\Delta t$), may be represented as:

$$\Delta t = m * \frac{P_1}{k}$$

Where m<k and k>1, and m is the index of the pulse being emitted and varies from 1 to k. PRP ($n*P_1$) positions the imaging pulse in a given cycle of the modulation wave 202, and the pulse delay ($m*P_1/k$) positions the imaging pulse within the given cycle to capture the microbubble at a given state in its oscillation cycle. As such, n and k are defined in order to synchronize the imaging pulse with the modulation wave and detect the reflected signal, where n corresponds to the number of full modulation wave periods between every acquisition, and k is the number of sampled microbubble oscillation sates over a full period of the modulation wave. While n is an integer, k and m may be non-integers or integers, depending on practical implementation.

In the example of FIG. 2, positions $204_1$-$204_5$ represent instances in time of the modulation wave when the microbubbles 124 are sampled, i.e. when an ultrasonic pulse is emitted and the reflections from the microbubbles 124 are detected. Based on the assumption that the microbubbles 124 will oscillate linearly over time, sampling the microbubble 124 at position $204_1$ of the modulation wave 202 will result in a detected signal of a same amplitude as sampling the microbubbles 124 at position $204_3$ of the modulation wave 202.

FIG. 3A illustrates an example of a reconstructed oscillation cycle of a microbubble using a plurality of reflections over time, where each position $304_1$-$304_5$ represents the size of the microbubble when sampled at a corresponding time $204_1$-$204_5$ of the modulation wave 202, respectively. The microbubble is shown to oscillate at a frequency $F_3$:

$$F_3 = \frac{1}{kPRP + \Delta t}$$

The microbubble is said to be in a rarefaction state (e.g. $304_2$) when its diameter is larger than at its equilibrium state (e.g. $304_3$), and in a compression state (e.g. $304_4$) when its diameter is smaller than its equilibrium state. The backscattered signal from the microbubble will be higher for a microbubble having a volume greater than its equilibrium state than a microbubble having a volume smaller than its equilibrium state. The reflected signal will thus depend on the volumetric oscillation state of the microbubbles which in turn is related to the local pressure field intensity. Due to this phenomenon, the microbubbles will therefore serve as pressure sensors throughout the medium and will indicate whether, at a given location, the medium is subjected to the pressure field of treatment. Knowing that the backscattered signal of the tissue over time should stay constant, the microbubble can be differentiated from the tissue by the variability of the signal in the slow time dimension.

Figure 3F:
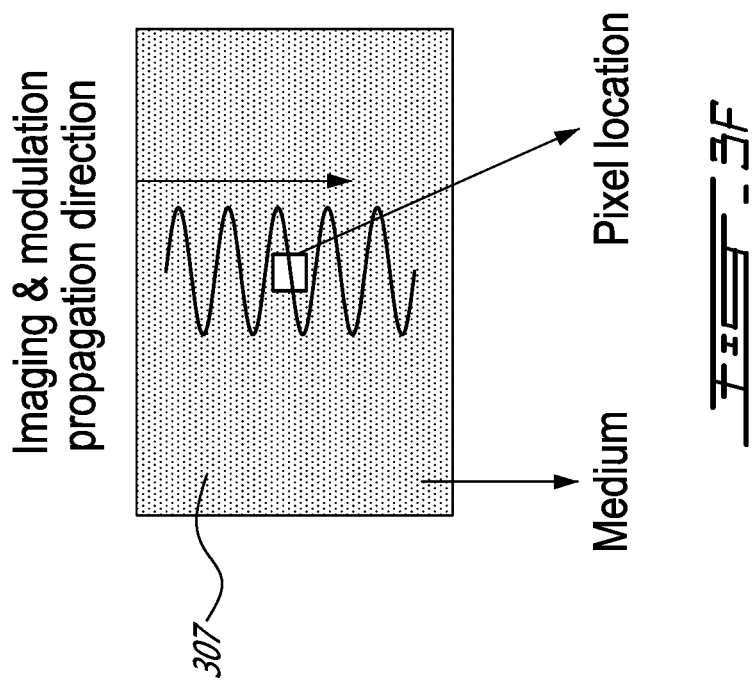

Referring to FIGS. 3B-3F, an example is illustrated for k=4. FIG. 3B shows a continuous modulation wave 301. "Slow time" is defined as the time from pulse to pulse, "fast time" is defined as the time along the depth dimension, and "relative slow time" is defined as the time in the slow time dimension relative to the time between modulation state samples (i.e. along the modulation wave period). FIG. 3C illustrates the relative position of the modulation wave 301 (shown as $301_A$-$301_E$) with respect to the imaging timing of a pixel in the medium. Line 302 shows the relative imaging timing for a random pixel location. FIG. 3D shows the intensity variation of signal 303, which represents a pixel containing tissue along the slow time and slow time relative to the modulation wave period (represented in the time domain). Also shown in FIG. 3D is the intensity variation of signal 308, which represents a pixel containing microbubbles along the slow time and slow time relative of the modulation wave period (represented in the time domain). FIG. 3E illustrates the frequency component 305 of a pixel containing tissue along the slow time (represented in the frequency domain) and the frequency component 306 of a pixel containing microbubble along the slow time (represented in the frequency domain). In FIG. 3F, there is shown a beam formed image 307 of the location of the pixel relative to the direction of propagation of the imaging and modulation waves.

The desynchronization of the propagation of the modulation wave (301A-301E) relative to the imaging pulse timing (302) through the additional delay $\Delta t$ allows extraction of the microbubble signal from the tissue clutter space (as shown with frequency components 305, 306). For each pixel (position) in the beamformed image 307, a Fourier analysis, or other methods such as short-time Fourier Transform, Wavelets Transform, Non-uniform discrete Fourier transform, etc., can be performed for all corresponding pixels in the same buffer along the slow time in order to compute the power spectrum of the pixel intensity oscillation. Given that the microbubbles will be imaged at different states along its oscillation period, the pixel intensity containing the microbubbles should vary accordingly (as shown at 308) compared to the tissue (as shown at 303) that should stay constant. A bandpass filter around the frequency 306 corresponding to that microbubble's oscillation can be applied to reject artefactual signal. The power spectrum can be integrated to build the acoustic map of the modulation ultrasound pressure profile.

In some embodiments, a Fourier analysis is performed for all corresponding pixels of the reconstructed images along the slow-time. Depending on the frequency of interest, the corresponding Fourier coefficient can be selected, resulting in an intensity map. The magnitude of the Fourier coefficients in each pixel characterizes the amplitude of the sinusoidal signal at the selected frequency in the backscattered signal and this value can then be translated and interpreted in pressure intensity, thus characterizing the pressure field intensity across the field of view. The simplicity of this method facilitates the implementation for real-time monitoring and can be tailored to different modulation frequencies and imaging probes.

In accordance with the above, the microbubbles 124 around the target 102 act as acoustic micro-sensors that indicate whether or not a specific location in the body 104 is subjected to the modulation wave and its intensity. As the modulation wave is, in certain applications, a treatment beam, the location of the treatment beam may be determined in real-time, during treatment by reconstructing a series of images where the reflection signals vary at a given frequency.

In some embodiments, X sets of Y images are acquired. Each detection of a reflection produces an image Y, and the Y images are grouped into X sets. For example, one set of images may comprise 250 images (the M images), acquired with 50 repetitions of 5 ultrasound pulses centered at frequency $F_2$ and having a pulse interval of $n*P_1+P_1/k$, where k=5. In some embodiments, k is kept to a low value to avoid having pulse intervals that are too long, for example k<10. These values are exemplary only and may vary.

Each set of Y images may be analysed independently. The X sets of Y images may then be used to generate a global image of the position of the ultrasound wave over time. A set of Y consecutives beamformed images are analysed using a Fourier transform over the slow time (similar to a Spectral Doppler Analysis) to compute the Frequency distribution of the resonating media (i.e., microbubbles acoustic sensors). The power of the resonating media (i.e., microbubbles) is computed by integration of the frequency components corresponding to the microbubbles for each pixel in the beamformed images and gives a mapping proportional to the pressure field of the modulation probe.

In some embodiments, the methods described herein may be used to: adjust the focal position in real time of a treatment beam; monitor stable cavitation of the microbubbles spatially and for frequency; monitor inertial cavitation of the microbubbles; monitor inertial cavitation of the microbubbles spatially and for frequency; quantify pressure at a given location after calibration with a hydrophone; and define ultrasound field profiles to validate a sequence of imaging and treatment in vitro.

Figure 4A:
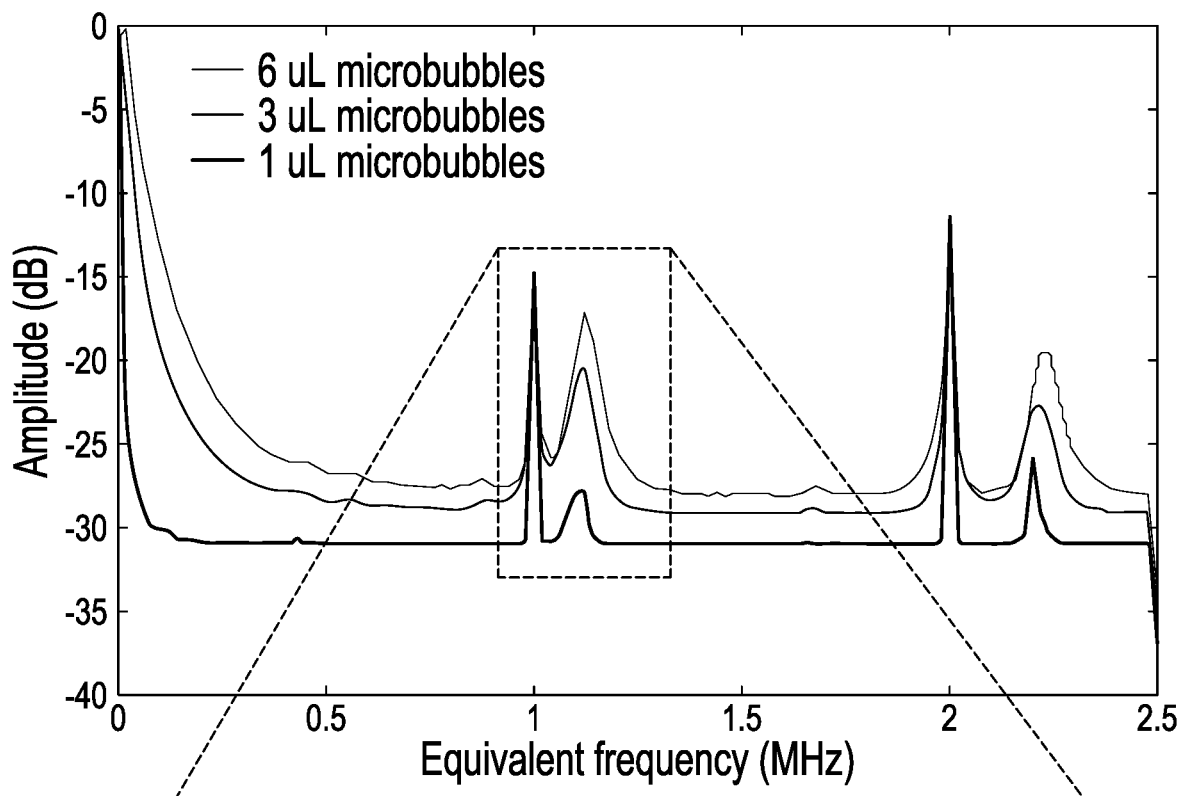
FIGS. 4A-4D are graphs showing a mean slow-time frequency spectrum at an equivalent sampling frequency for every pixel of a field of view.
Figure 4B:
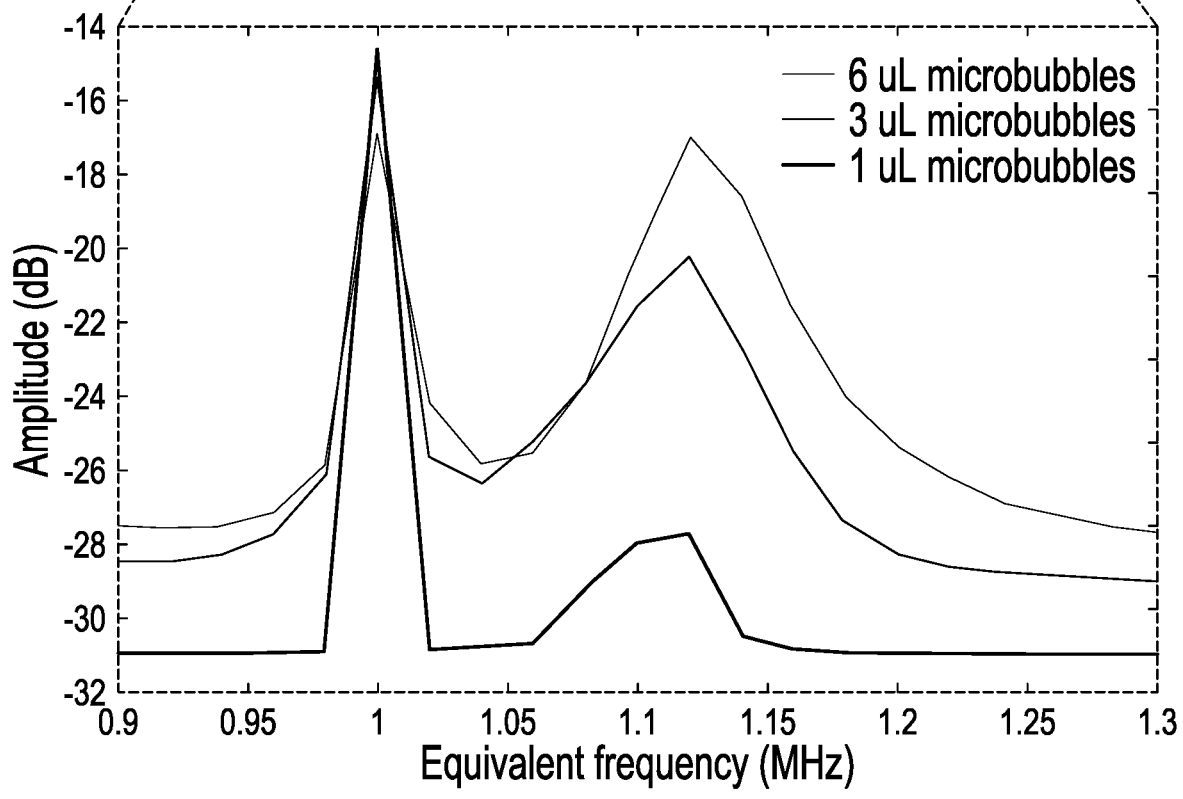
Figure 4C:
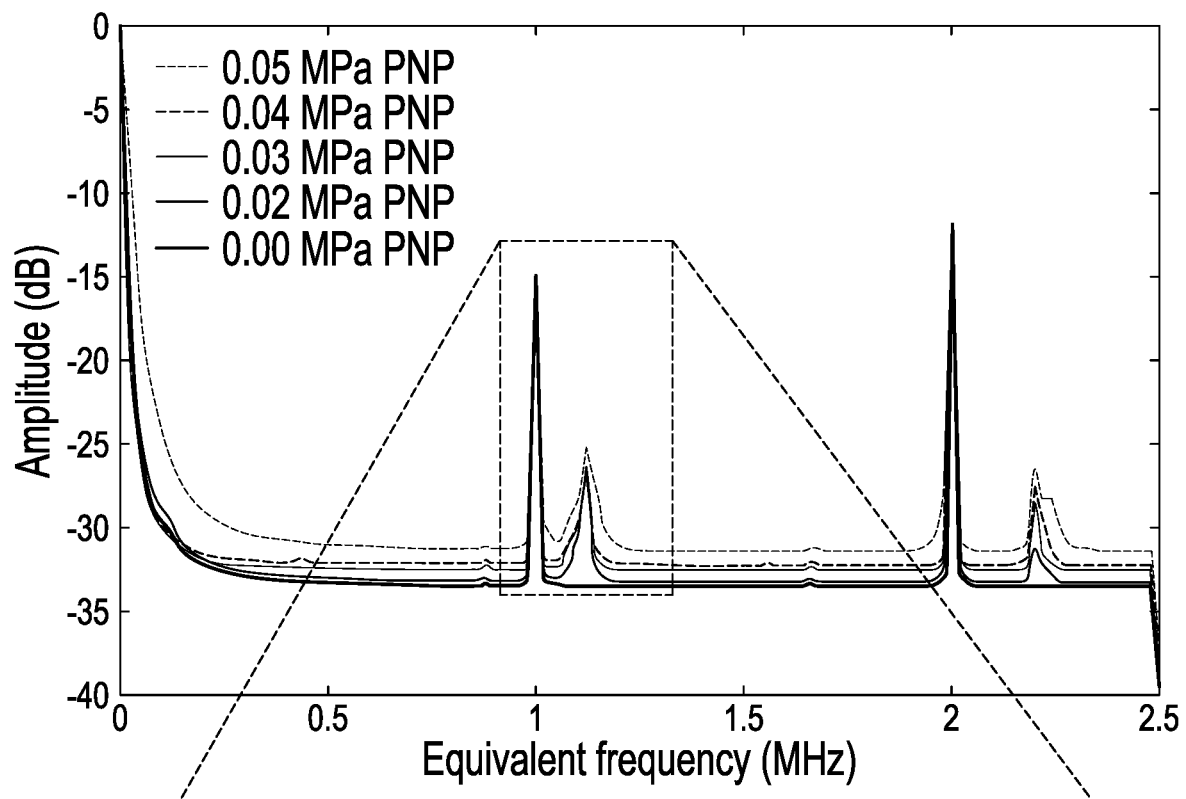
Figure 4D:
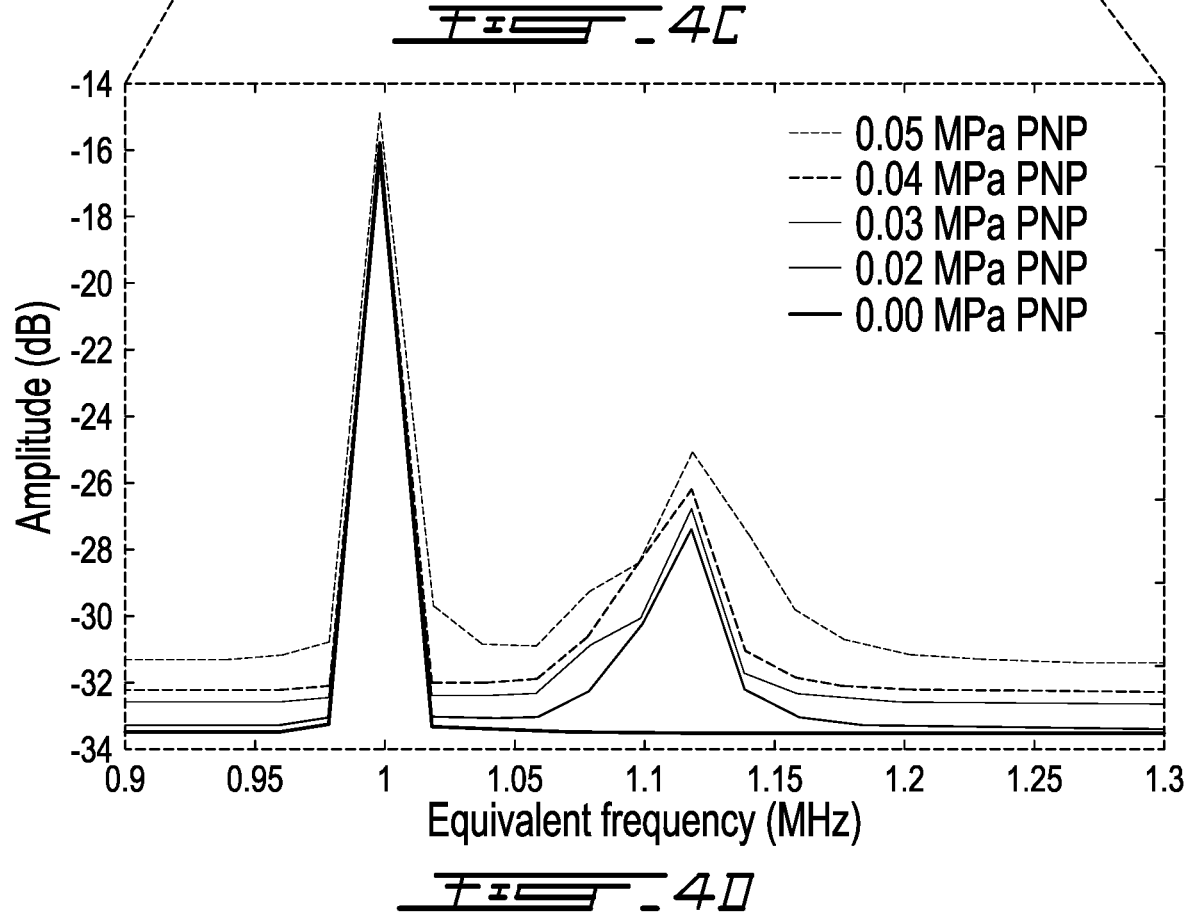

The methods and systems described herein may be used to show the intensity of the pressure field through the intensity of pixels visualized in the resulting filtered image. However, as the microbubble concentration increases, the pixel intensity also increases under the same modulation conditions. FIGS. 4A-4D show a mean slow-time frequency spectrum at the equivalent sampling frequency for every pixel of the field of view. FIG. 4A shows spectrum profiles at different microbubble concentrations under the same high intensity focused ultrasound modulation (around 0.1 MPa). FIG. 4B is a zoomed in spectrum of FIG. 4A between 0.9 MHz and 1.3 MHz. FIG. 4C shows spectrum profiles at variable high intensity focused ultrasound peak negative pressure amplitudes with a constant microbubble concentration. FIG. 4D is a zoomed in spectrum of FIG. 4C between 0.9 MHz and 1.3 MHz. As shown in FIG. 4A, the microbubble concentration influences the amplitude of the signal around the frequency of interest. This condition makes certain tests harder to accomplish because of the inherent effect of the microbubble concentration on the results, which should be precisely standardized in between testing conditions in order to see the pressure/intensity relation without a microbubble concentration bias. FIG. 4C shows that the method is sensitive to changes in the intensity of the modulation wave. A relationship is shown between the amplitude of the microbubble oscillation through the value of the Fourier coefficient and the detected reflections at the frequency of interest. The characterization in free field allows the frequency of interest of cavitating microbubbles to be determined, and to determine the response of the modality when no modulation wave is sent through the medium. As FIG. 4C shows, a spike around the 1-MHz band is constant regardless of the modulation intensity, indicating that the microbubble oscillation frequency does not correspond to the expected frequency of 1 MHz, which is a HIFU driving frequency. The volumetric oscillation frequency of the microbubbles corresponds to a signal around the 1.12 MHz band, and the intensity of the corresponding signal depends on the modulation transducer output.

The validity of the pressure mapping using the method described herein was evaluated by comparing the resulting compounded map to the pressure mapping obtained using hydrophone measurements performed in the mid plane of the focal field. FIG. 5A shows the overall FOV starting at 77 mm from the imaging probe with an hourglass-like shaped pressure field, with a zoomed in region in a bottom right hand corner of the image corresponding to the same region as the hydrophone measurement. FIG. 5B illustrates a 2D central plane of the hydrophone pressure map. FIGS. 5C and 5D show the close resemblance between the mean profiles measurements of the two mapping techniques along the HIFU axial direction. Both these profiles show similar dips around the central peak as expected for a focused ultrasound focal pressure profile. The dependency obtained between the corresponding pixel intensity value of the method described herein and the measured pixel negative pressure shown in FIG. 5D gives a linear correlation with an R-square of 0.7906. In order to have the same number of data points between the two datasets, the image of FIG. 5A was down sampled to the size of the hydrophone map (as per the inset).

To assess the capability to isolate the microbubble cavitation signal from a soft-tissue-like medium, a tissue-mimicking phantom was placed on the left side of the field of view. FIG. 7(a-b) attests to our method's capability to allow tissue suppression and enhance the microbubble signal compared to a regular B-mode image of the same field of view. The phantom and the coupling cone artefact signals are mostly filtered out, resulting in only the pressure field mapping. The focal region of the pressure field seen in FIG. 7(a) appears to have a focal dimension corresponding with the theoretical focal size (focal length 10.21 mm×focal width 1.37 mm at $F_0$). The intensity profile (FIG. 7(c)) along the blue dotted line shows the lack of signal on the left side of the image where the phantom was standing, causing the absence of microbubble and thus a cavitation signal. This demonstrates that without microbubbles acting as local pressure sensors, the pressure field cannot be characterized in those regions.

Another test performed to assess the method was to place a tissue-mimicking phantom on the left side of the field of view. FIGS. 6A-6C attest to the method's capability to allow tissue suppression and enhance the microbubble signal (shown in FIG. 6A) compared to a regular B-mode image of the same field of view (shown in FIG. 6B). The phantom and the coupling cone artefact signals are mostly filtered out, resulting in only the pressure field mapping. The focal region of the pressure field seen in FIG. 6A appears to have a focal dimension corresponding with the theoretical focal size (focal length 10.21 mm×focal width 1.37 mm at $F_0$). The intensity profile FIG. 6C is taken along line 1002 of FIG. 6A and shows the lack of signal on the left side of the image where the phantom was standing, causing the absence of microbubble and thus the absence of a cavitation signal. This demonstrates that without microbubbles acting as local pressure sensors, the pressure field cannot be characterized in those regions.

The effect of gravity-generated flow on the method modality was also evaluated and is demonstrated in FIGS. 7A-7C. In order to have a better view of the pressure field inside the vessel, the imaging was performed along a longitudinal cut of a ~5 mm diameter vessel. FIG. 7A is a pressure field mapping for the present method, FIG. 7B is a pressure field mapping using B-mode imaging. As shown in FIG. 7A, the compounded pressure map obtained characterizes the pressure field inside the vessel as microbubbles flow through it. Most of the signal is limited to the inside of the vessel and has the expected focal profile similar to the one in the free field. The presence of speckle-like signals outside of the vessel can be explained by the presence of small gas pockets in the phantom medium. FIG. 7C illustrates a pixel intensity profile in decibels. Curve 706 was taken along line 702 of FIG. 7A, curve 708 was taken along line 704 of FIG. 7A.

Figure 8G:
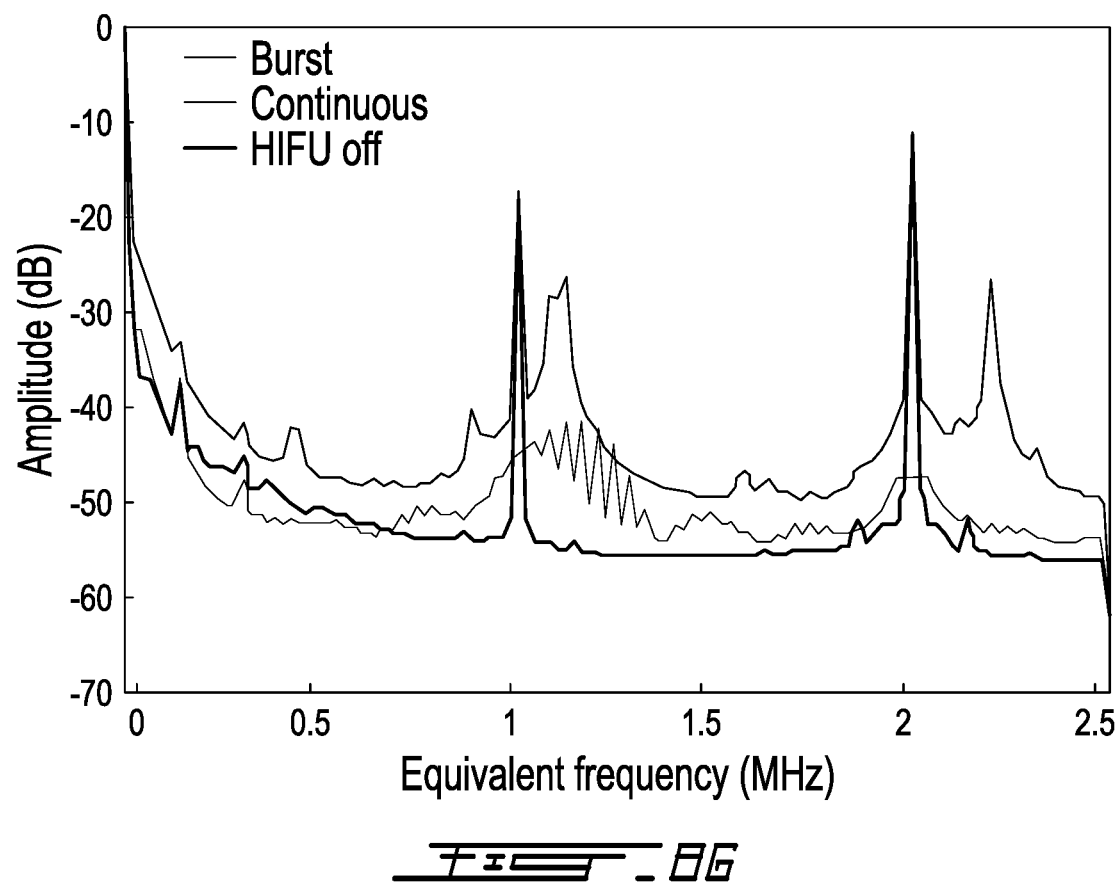
Figure 8H:
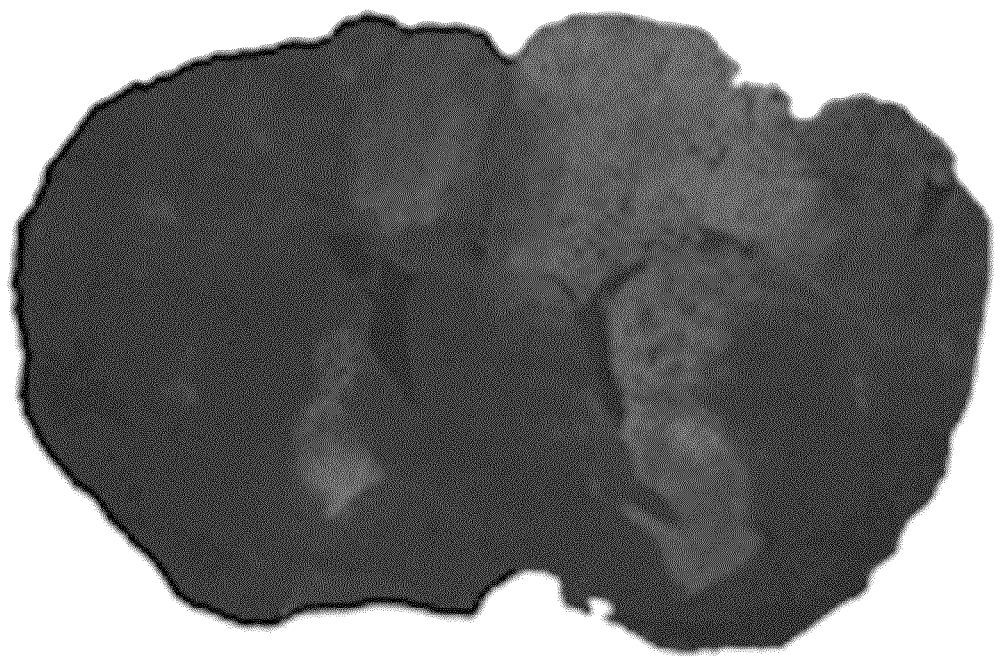

FIGS. 8A-H show the initial proof of concept of the imaging modality in vivo in the brain of an anesthetized mouse without craniotomy. Compounded pressure field mapping images of continuous and burst high intensity focused ultrasound blood-brain barrier (BBB) opening treatment on the right and left side of the brain, respectively, are shown. FIG. 8A is a full field of view of the compounded pressure field mapping of continuous high intensity focused ultrasound exposure treatment for the right side of the brain. Region 804 shows the theoretical focal size and position of the H-102 transducer in relation to the imaging probe. FIG. 8B is an overlay of the corresponding histology section with the zoomed in compounded pressure field mapping of region 802. Curve 806 shows the normalized acoustic energy integration along the axial dimension. FIG. 8C is a B-mode reference of the same field of view as FIG. 8A. FIG. 8D is a full field of view of the compounded pressure field mapping of continuous high intensity focused ultrasound exposure treatment for the left side of the brain. FIG. 8E is an overlay of the corresponding histology section with the zoomed in compounded pressure field of region 810. Curve 812 shows the normalized acoustic energy integration along the axial dimension. FIG. 8F is a B-mode reference of the same field of view as FIG. 8D. FIG. 8G shows mean frequency spectrum profiles of the measured signal for burst and continuous treatment for mouse blood-brain barrier opening. FIG. 8H is a fluorescence microscopy of a representative coronal brain section stained with Evans Blue dye.

Higher intensity regions in maps were observed to be overlapping with the corresponding BBB opened region as shown by auto-fluorescence of Evan's blue that was injected in the tail vein simultaneously to microbubbles. However, the signals were not detected for deeper structures in the burst treatment. The normalized integrated acoustic energy 806, 812 shown in FIGS. 8B and 8E, respectively, indicates that the theoretical focal area 804, 808 might not be where the amount of acoustic energy is the highest, demonstrating the importance of this kind of imaging modality. This variation may be caused by beam deformation due to the skull, standing waves, and potentially, other biological effects. Further analysis of the average frequency spectrum profiles in the region of interest across all ensembles of a dataset shown in FIG. 9G reveals an increase of base signal level between the burst treatment and the continuous one, as well as the presence of different frequency spikes compared to in vitro testing done at lower peak negative pressure (PNP). Ultra and sub-harmonic signals were present in the continuous treatment profile as well as an increase in the base signal. Accordingly, BBB opening has been confirmed on both sides by imaging of Evan's blue fluorescence (excitation at 620 nm, emission at 680 nm) while evidence for brain damage is provided by the presence of erythrocyte extravasation at the right cerebral hemisphere, which received a 0.40 MPa PNP continuous focused ultrasound treatment.

In some embodiments, the ultrasound images can be generated using a computing device 900 as illustrated in FIG. 9. It should be noted that the computing device 900 may be implemented as part of the imaging device 106, part of the modulation wave generator 110, or separately therefrom. In some embodiments, the modulation wave generator 110 and the imaging device 106 are implemented as one device by the computing device 900. In some embodiments, the computing device 900 is within the imaging device 106 and cooperates with other hardware and/or software components therein. In such cases, the imaging device 106 generates the ultrasound images based on the detected reflections of the ultrasound pulses as captured by the probe 108.

The computing device 900 comprises a processing unit 904 and a memory 904 which has stored therein computer-executable instructions 906. The processing unit 902 may comprise any suitable devices configured to cause a series of steps to be performed such that instructions 906, when executed by the computing device 900 or other programmable apparatus, may cause functions/acts/steps described herein to be executed. The processing unit 902 may comprise, for example, any type of general-purpose microprocessor or microcontroller, a digital signal processing (DSP) processor, a CPU, an integrated circuit, a field programmable gate array (FPGA), a reconfigurable processor, other suitably programmed or programmable logic circuits, or any combination thereof.

The memory 904 may comprise any suitable known or other machine-readable storage medium. The memory 904 may comprise non-transitory computer readable storage medium, for example, but not limited to, an electronic, magnetic, optical, electromagnetic, infrared, or semiconductor system, apparatus, or device, or any suitable combination of the foregoing. The memory 904 may include a suitable combination of any type of computer memory that is located either internally or externally to device, for example random-access memory (RAM), read-only memory (ROM), electro-optical memory, magneto-optical memory, erasable programmable read-only memory (EPROM), and electrically-erasable programmable read-only memory (EEPROM), Ferroelectric RAM (FRAM) or the like. Memory 904 may comprise any storage means (e.g., devices) suitable for retrievably storing machine-readable instructions 906 executable by processing unit 902.

With reference to FIG. 10, there is illustrated an example method 1000 for generating ultrasound images, as performed, for example, using the setup 100. At step 1002, a modulation wave is applied to a target in a body having received an injection of microbubbles through a fluid. The modulation wave has a fixed frequency $F_1$ and a period $P_1$. The modulation wave comprises a high intensity focused ultrasound (HIFU) that causes the microbubbles to undergo stable acoustic cavitation. At step 1004, ultrasound pulses are emitted concurrently with the application of the HIFU modulation wave. The ultrasound pulses are centered at a frequency $F_2$ and have a pulse repetition period of $n*P_1$ and a pulse delay of $m*P_1/k$, where $m<k$ and $k>1$, where the pulse delay varies with m, where n is an integer, and where m and k may be integers or non-integers. As steps 1002 and 1004 are performed concurrently, the order illustrated in the method 1000 may be inverted.

At step 1006, reflections of the ultrasound pulses by the microbubbles and the surrounding medium are detected after each emission, for a duration corresponding to a depth of the target. At step 1008, ultrasound images are formed from the reflections.

The method 1000 may be used for the active mapping of cavitation events. By delaying plane wave emissions with a predetermined fraction of the HIFU period, the pressure field may be mapped. Promising in vivo results shown herein demonstrate the feasibility of the method 1000 in the context of BBB opening monitoring. In vivo imaging maps based on the method 1000 suggest that the method 1000 could be used to detect the position of the HIFU beam and also signal the possible inertial cavitation events correlated with damage.

The frequency spectra obtained from testing display two prominent peaks, one at the driving frequency and the other at 1.12 MHz. The first peak was found to be associated with interpolation errors in the beamforming algorithm and could be further reduced by increasing the sampling frequency. The pressure maps obtained in the free field showed a good correlation between the pixel intensity using the method 1000 and the pixel intensity using hydrophone pressure measurements. These results indicate that the method 1000 could be used as a rapid approach to transducer characterization since a single acquisition of a few seconds after mixing microbubbles in a water tank can be used to map entire fields of view. The method 1000 may also be generalized to 3D imaging by using 2-D matrix arrays. Additionally, pressure maps may be generated in the presence of a static tissue phantom and in presence of flow, indicating that the approach may also be applied in contexts where it is not possible to perform hydrophone measurements. Finally, the tissue filtering capabilities of the method 1000 may also be used in the context of contrast-enhanced ultrasound imaging.

Active pressure field mapping has been shown possible in vivo during continuous and burst HIFU-induced BBB opening. Frequency spectra also appear to show inertial cavitation can be detected during continuous treatment via a higher broad-band signal compared to burst treatment where no noticeable erythrocyte extravasation is observed.

It will be understood that the setup used for performing the method 1000 may be modified. For example, the distance between the imaging probe 108 and the region of interest (e.g. the target 102) may vary and the number of elements used in the probe 108 may vary. These parameters may have an impact on resolution and thus imaging quality, especially when the method 1000 is performed in vivo. In some embodiment, the probe 108 may include an imaging transducer lowered into a larger diameter focused ultrasound transducer, allowing the imaging probe 108 to be closer to the target 102 and increasing the resolution. In some embodiments, 3D imaging based on a 2-D matrix-array probe may be used with the method 1000. In some embodiments, the sequence used in vivo for burst treatment may be synchronized to the bursts themselves. Triggering the imaging on focused ultrasound burst train output could improve the slow time signal reconstruction and optimize the data acquisition.

The method 1000 may provide several benefits in comparison to other methods. For example, as this method relies on the fundamental resonance frequency, the possible signal gain is better than using a nonlinear response, as more energy is included in the fundamental frequency band compared to nonlinear frequency bands. A nonlinear response also increases the risk of the microbubble rupture (i.e. inertial cavitation). Furthermore, the method 1000 doesn't require frequency locking and could also be used with different transducer assortments. The method 1000 therefore allows for different imaging probe frequencies and combinations, which can vary depending on the experimental or clinical application.

Parts or all of the method 1000 may be implemented in a high level procedural or object oriented programming or scripting language, or a combination thereof, to communicate with or assist in the operation of a computer system, for example the computing device 900. Alternatively, parts or all of the method 1000 may be implemented in assembly or machine language. The language may be a compiled or interpreted language.

Embodiments of the method 1000, in whole or in part, may also be considered to be implemented by way of a non-transitory computer-readable storage medium having a computer program stored thereon. The computer program may comprise computer-readable instructions which cause a computer, or more specifically the processing unit 902 of the computing device 900, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the systems and methods described herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be apparent to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for ultrasound imaging comprising:
applying a continuous ultrasound modulation wave at a fixed frequency $F_1$ and a period $P_1$ to a target in a body, the body having received an injection of microbubbles through a fluid, the modulation wave causing the microbubbles to undergo stable acoustic cavitation, the modulation wave being a treatment beam;
emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, and where n and k are defined to synchronize the ultrasound imaging pulses with the continuous modulation wave by positioning each ultrasound imaging pulse within a given cycle of the continuous modulation wave;

detecting reflections of the ultrasound imaging pulses by the microbubbles after each emission for a duration corresponding to a maximum depth of the target; and forming ultrasound images from the reflections to determine, based on the ultrasound images, a position of the treatment beam in real-time.

2. The method of claim 1, wherein forming the ultrasound images comprises performing a Fourier analysis in slow time to compute a power spectrum of pixel intensity oscillation.

3. The method of claim 1, wherein the modulation wave is a high intensity focused ultrasound (HIFU).

4. The method of claim 1, wherein the body is an organ.

5. The method of claim 1, wherein forming the ultrasound images comprises forming X sets of Y images, where each detection of a reflection produces one of the images Y, and the Y images are grouped into the X sets.

6. The method of claim 5, further comprising generating a global image of the position of the treatment beam over time from the X sets of Y images.

7. The method of claim 1, wherein k<10.

8. The method of claim 1, wherein forming the ultrasound images comprises forming the ultrasound images in real-time and displaying the ultrasound images.

9. The method of claim 8, further comprising displacing the treatment beam from a first position to a second position, and confirming the displacing from updated ultrasound images.

10. The method of claim 2, wherein a magnitude of Fourier coefficients in each pixel of the ultrasound images characterizes an intensity of a local pressure field generated by the treatment beam.

11. An imaging system comprising:

a modulation wave generator coupled to an ultrasound transducer configured for emitting a continuous ultrasound modulation wave at a fixed frequency $F_1$ and a period $P_1$ to a target in a body, the body having received an injection of microbubbles through a fluid, the modulation wave causing the microbubbles to undergo stable acoustic cavitation, the modulation wave being a treatment beam; and an imaging device coupled to at least one probe and configured for:

emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, and where n and k are defined to synchronize the ultrasound imaging pulses with the continuous modulation wave by positioning each ultrasound imaging pulse within a given cycle of the continuous modulation wave;

detecting reflections of the ultrasound imaging pulses by the microbubbles after each emission for a duration corresponding to a maximum depth of the target; and forming ultrasound images from the reflections to determine, based on the ultrasound images, a position of the treatment beam in real-time.

12. The imaging system of claim 11, wherein forming the ultrasound images comprises performing a Fourier analysis in slow time to compute a power spectrum of pixel intensity oscillation.

13. The imaging system of claim 12, wherein a magnitude of Fourier coefficients in each pixel of the ultrasound images characterizes an intensity of a local pressure field generated by the treatment beam.

14. The imaging system of claim 11, wherein the modulation wave is a high intensity focused ultrasound (HIFU).

15. The imaging system of claim 11, wherein the body is an organ.

16. The imaging system of claim 11, wherein forming the ultrasound images comprises forming X sets of Y images, where each detection of a reflection produces one of the images Y, and the Y images are grouped into the X sets.

17. The imaging system of claim 16, wherein the imaging device is further configured for generating a global image of the position of the treatment beam over time from the X sets of Y images.

18. The imaging system of claim 11, wherein k<10.

19. The imaging system of claim 11, wherein forming the ultrasound images comprises forming the ultrasound images in real-time and displaying the ultrasound images.

20. A method for applying a treatment beam to a subject, the method comprising:

applying the treatment beam as a continuous ultrasound modulation wave at a fixed frequency $F_1$ and a period $P_1$ to a target in the subject, the subject having received an injection of microbubbles through a fluid, the modulation wave causing the microbubbles to undergo stable acoustic cavitation;

emitting, toward the target and concurrently with the modulation wave, ultrasound imaging pulses centered at a frequency $F_2$ and having a pulse repetition period of $n*P_1$ and a pulse delay of $m*P_1/k$, where the pulse delay varies with m, m<k, and k>1, and where n and k are defined to synchronize the ultrasound imaging pulses with the continuous modulation wave by positioning each ultrasound imaging pulse within a given cycle of the continuous modulation wave;

detecting reflections of the ultrasound imaging pulses by the microbubbles after each emission for a duration corresponding to a maximum depth of the target;

forming ultrasound images from the reflections to determine, based on the ultrasound images, a location of the treatment beam in real-time;

displaying the ultrasound images as the treatment beam is applied; and adjusting the location of the treatment beam based on the ultrasound images.

* * * * *